United States Patent [19]
Mojsov et al.

[11] Patent Number: 5,882,899
[45] Date of Patent: Mar. 16, 1999

[54] RECEPTOR FOR PEPTIDE HORMONES INVOLVED IN ENERGY HOMEOSTASIS, AND METHOD AND COMPOSITIONS FOR USE THEREOF

[75] Inventors: Svetlana Mojsov; Yang Wei, both of New York, N.Y.

[73] Assignee: The Rockefeller University, New York, N.Y.

[21] Appl. No.: 76,651

[22] Filed: May 12, 1998

Related U.S. Application Data

[60] Division of Ser. No. 538,816, Oct. 3, 1995, which is a continuation-in-part of Ser. No. 437,466, May 9, 1995, abandoned.

[51] Int. Cl.[6] .............................. G01N 33/53; C12Q 1/70; C07K 14/00
[52] U.S. Cl. ................................. 435/7.1; 435/4; 435/6; 435/7.2; 435/7.8; 530/350
[58] Field of Search .................................. 435/6, 7.1, 7.2, 435/7.8; 530/350

[56] References Cited

PUBLICATIONS

Adamou et al. (1995) Biochem. Biophys. Res. Comm. 209:385–92.
Christophe, 1993, *Biochim. Biophys. Acta* 1154:183–199.
Couvineau et al., 1994, *Biochem. Biophys. Res. Comm.* 200:769–776.
Harmar et al. (1994) TiPS 15:97–9.
Hashimoto et al., 1993, *Neuron* 11:333–342.
Hosoya et al. (1993) Biochem. Biophys. Res. Comm. 194:133–43.
Inagaki et al. (1994) Proc. Natl. Acad. Sci. USA 91:2679–83.
Ishihara et al. (1992) Neuron 8:811–9.
Lutz et al. (1993) FEBS Letters 334:3–8.
McArdle, 1994, *Endocrinology,* 135:815–817.
Ogi et al., 1993, *Biochem. Biophys. Res. Comm.* 196; 1511–1521.
Segre and Goldrinr, 1993, *Trends Endocrinol. Metab.* 4:309–314.
Sreedharan et al. (1993) Biochem. Biophys. Res. Commun. 193:546–53.
Svoboda et al. (1994) Biochem. Biophys. Res. Commun. 205:1617–24.
Wei and Mojsov, 1995, *FEBS Lett.* 358:219–224.
Yada et al., 1994, *J. Biol. Chem.* 269:1290–1293.

*Primary Examiner*—Nancy Degen
*Assistant Examiner*—Sean McGarry
*Attorney, Agent, or Firm*—Klauber & Jackson

[57] ABSTRACT

The invention relates to an energy homeostasis peptide hormone receptor, and in particular, a second common PACAP/VIP receptor (PACAP/VIP R-2 or R-2B) cDNA expressed in human adipocytes. Pituitary adenylate cyclase activating polypeptide (PACAP) and vasoactive intestinal polypeptide (VIP) are two structurally related peptides with multiple physiological effects. The present receptor recognizes PACAP-38 and VIP with similar affinity and is coupled to the cAMP-mediated signal transduction pathway. Transcripts of the second common PACAP/VIP R-2 receptor are also found in human brain and in a number of peripheral tissues, such as pancreas, muscle, heart, lung, kidney, stomach and at low levels in the liver, while transcripts of PACAP/VIP R-2B are not found in pancreas, stomach or kidney. Comparison of the tissue distribution of PACAP/VIP R-2 to that of the other two types of PACAP receptors (PACAP-Type 1 and the other common PACAP/VIP R-1) by RNase protection shows that each of the three PACAP receptors is expressed in a unique set of human peripheral tissues. However, PACAP/VIP R-2 is receptor with broadest distribution in human tissues. Thus, some of the physiological effects of PACAP-38 and VIP in peripheral tissues, especially in pancreas and skeletal muscle, could be mediated through the energy homeostasis peptide hormone receptor, and particularly the second common PACAP/VIP receptor.

7 Claims, 21 Drawing Sheets

FIG. 1A

```
HPACAP/VIP R-2    1  MRTLLPPALLT--CWLLAPVNSIHPECRFHLEIQEEETKCAELLRSQTEK  48
                     ::    :  ::::  :    ::::::::::::::::::::::::: ::
MPACAP-3/RVIP-2   1  MRASVV---LTCYCWLLVRVSSIHPECRFHLEIQEEETKCAELLSSQMEN  47
                                  *                                 *

HPACAP/VIP R-2   49  HKACSGVWDNITCWRPANVGETVTVPCPKVFSNFYSKAGNISKNCTSDGW  98
                     : :::::::::::::  :::::::::::::::::: ::::::::::::
MPACAP-3/RVIP-2  48  HRACSGVWDNITCWRPADIGETVTVPCPKVFSNFYSRPGNISKNCTSDGW  97
                                                             TM1

HPACAP/VIP R-2   99  SETFPDFVDACGYSDPEDESKITFYILVKAIYTLGYSVSLMSLATGSIIL 148
                     ::::::: ::::::::::::::::::::::::::::::::::: :::::
MPACAP-3/RVIP-2  98  SETFPDFIDACGYNDPEDESKITFYILVKAIYTLGYSVSLMSLTTGSIII 147
                                              TM2

HPACAP/VIP R-2  149  CLFRKLHCTRNYIHLNLFLSFILRAISVLVKDDVLYSSSGTLHCPDQPSS 198
                     ::::::::::::::::::::: ::::::::::::::::::::  :: ::
MPACAP-3/RVIP-2 148  CLFRKLHCTRNYIHLNLFLSFMLRAISVLVKDSVLYSSSGTLRCHDQPGS 197
```

FIG. 1B

```
HPACAP/VIP R-2    199  WVGCKLSLVFLQYCIMANFFWLLVEGLYLHTLLVAMLPPRRCFLAYLLIG  248
                       ::::::::::::::::::::::::::::::::::::::::::::::::
MPACAP-3/RVIP-2   198  WVGCKLSLVFFQYCIMANFYWLLVEGLYLHTLLVAILPPSRCFLAYLLIG  247
                                                    TM3                    TM4  TM5

HPACAP/VIP R-2    249  WGLPTVCIGAWTAARLYLEDTGCWDTNDHSVPWWVIRIPILISIIVNFVL  298
                       ::  ::::  :::::  :::::::::::::::::::::::::  ::::
MPACAP-3/RVIP-2   248  WGIPSVCIGAWIATRLSLEDTGCWDTNDHSIPWWVIRMPILISIVVNFAL  297
                                             TM4                      TM6

HPACAP/VIP R-2    299  FISIIRILLQKLTSPDVGGNDQSQYKRLAKSTLLLIPLFGVHYMVFAVFP  348
                       ::::  ::::::::::::::::::::::::::::::::::::::::: ::
MPACAP-3/RVIP-2   298  FISIVRILLQKLTSPDVGGNDQSQYKRLAKSTLLLIPLFGVHYMVFAAFP  347
                                                                         TM7

HPACAP/VIP R-2    349  ISISSKYQILFELCLGSFQGLVVAVLYCFLNSEVQCELKRKWRSRCPTPS  398
                       ::::  ::::::: :::: ::::::::::::::::::::  :: : :
MPACAP-3/RVIP-2   348  IGISSTYQILFELCVGSFQGLVVAVLYCFLNSEVQCELKRRWRGLCLTQP  397

HPACAP/VIP R-2    399  ASRDYRVCGSSFSHNGSEGALQFHRASRAQSFLETQTSVI  437
                       :::::  ::::: :::::  ::  :::  :: :: :::::
MPACAP-3/RVIP-2   398  GSRDYRLHSWSMSRNGSESALQIHRGSRTQSFLQSETSVI  437
```

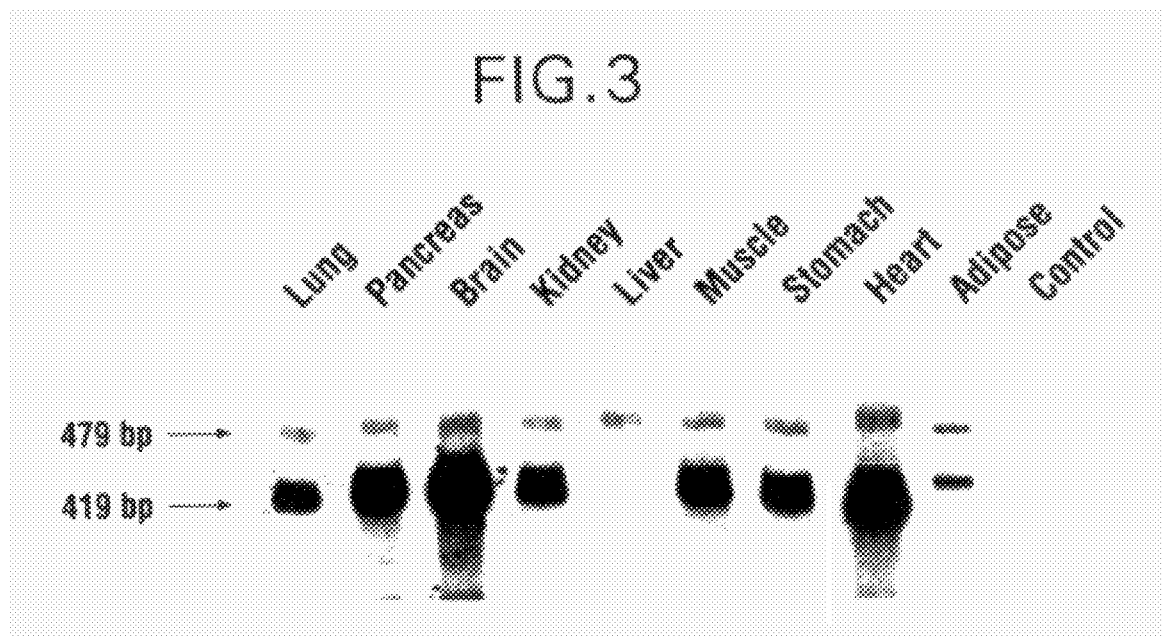

```
  1 GGGCCGGGAC GGAGGGGGCG GCCCCCGCGC TCGGGGCGCT CGGCTACAGC
 51 TGCGGGGCCC GAGGTCTCCG CGCACTCGCT CCCGGCCCAT GCTGGAGGCG
101 CGGAACCGCG GGGACCTAGG ACGGAGGCGG CGGGCGCTGG GGCGGCCCCC
151 GGCACGCTGA GCTCGGGATG CGGACGCTGC TGCCTCCCGC GCTGCTGACC
201 TGCTGGCTGC TCGCCCCCGT GAACAGCATT CACCCAGAAT GCCGATTTCA
251 TCTGGAAATA CAGGAGGAAG AAACAAAATG TGCAGAGCTT CTGAGGTCTC
301 AAACAGAAAA ACACAAAGCC CTAATGTGGG AGAGACCGTC ACGGTGCCCT GCCCAAAAGT
351 TGGCGGGCCTG GTCAGAGACG TTCCCAGATT AAGCAGGAAA CATAAGCAAA AACTGTACGA
401 CTTCAGCAAT TTTTACAGCA AAGCAGGAAA TTCCCAGATT TCGTCGATGC CTGTGGCTAT
451 GTGATGGATG GTCAGAGACG TTCCCAGATT CAAGATCACG TTTTATATTC TGGTGAAGGC
501 AGCGACCCGG AGGATGAGAG CAAGATCACG GTGTCTCTCT GATGTCTCTT GCAACAGGAA
551 CATTTATACC CTGGGCTACA GTGCCTCTTC AGGAAGCTGC ACTGCACCAG GAATTACATC
601 GCATAATTCT GTGCCTCTTC AGGAAGCTGC ACTGCACCAG AGAGCCATCT CAGTGCTGGT
651 CACCTGAACC TGTTCCTGTC CTTCATCCTG AGAGCCATCT CAGTGCTGGT
701 CAAGGACGAC GTTCTCTACT CCAGCTCTGG CACGTTGCAC TGCCCTGACC
```

FIG.6A

```
 751  AGCCATCCTC CTGGGTGGGC TGCAAGCTGA GCCTGGTCTT CCTGCAGTAC
 801  TGCATCATGG CCAACTTCTT CTGGCTGCTG GTGGAGGGGC TCTACCTCCA
 851  CACCCTCCTG GTGGCCATGC TCCCCCCTAG AAGGTGCTTC CTGGCCTACC
 901  TCCTGATCGG ATGGGGCCTC CCCACCGTCT GCATCGGTGC ATGGACTGCG
 951  GCCAGGCTCT ACTTAGAAGA CACCGGTTGC TGGGATACAA ACGACCACAG
1001  TGTGCCCTGG TGGGTCATAC GAATACCGAT TTTAATTTCC ATCATCGTCA
1051  ATTTTGTCCT TTTCATTAGT ATTATACGAA TTTTGCTGCA GAAGTTAACA
1101  TCCCCAGATG TCGGCGGCAA CGACCAGTCT CAGTACAAGA GGCTGGCCAA
1151  GTCCACGCTC CTGCTTATCC CGCTGTTCGG CGTCCACTAC ATGGTGTTTG
1201  CCGTGTTTCC CATCAGCATC TCCTCCAAAT ACCAGATACT GTTTGAGCTG
1251  TGCCTCGGGT CGTTCCAGGG CCTGGTGGTG GCCGTCCTCT ACTGTTTCCT
1301  GAACAGTGAG GTGCAGTGCG AGCTGAAGCG AAAATGGCGA AGCCGGTGCC
1351  CGACCCCGTC CGCGAGCCGG GATTACAGGG TCTGCGGTTC CTCCTTCTCC
1401  CACAACGGCT CGGAGGGCGC CCTGCAGTTC CACCGCGCGT CCCGAGCCCA
```

```
1451  GTCCTTCCTC CAAACGGAGA CCTCGGTCAT CTAGCCCCAC CCCTGCCTGT
1501  CGGACGCGGC GGGAGGCCCA CGGTTCGGGG CTTCTGCGGG GCTGAGACGC
1551  CGGCTTCCTC CTTCCAGATG CCCGAGCACC GTGTCGGGCT GGTCAGCGCG
1601  GTCCTGACTC CGTCAAGCTG GTTGTCCACT AAACCCCATA CCTGGAATTG
1651  GAGTCGTGTT GTCATTGACT CAACTTAAAC TCCAGCACCA CGACCCTGCT
1701  GCTATCTCGC ACCTGAAACA AGCTAACATG ACTAACACCC TTAATTCCAT
1751  CCACCCTCCT CTCCCTAGGA GGCCTGCGCC CGCTAACCGG CTTTTTCGCA
1801  AATGGGCCAT TATCGAA
```

```
  1  GGGGAGCGGG GTCGCCCGGG GTCCGGAGCT TCCTCCCGGA GAGCGTGAAG
 51  CGCTGAGCTC CGGTCCCGCC GGTTGCCGAC TCGGGTTGGG AGGCTGCCTG
101  CGCCCTTCCC CGCGCCCCAC CGTCCGGGGT TTGCTGGAAA CGGGATCGTT
151  TCTTCCTGGA CGCGTCAACG ATGAGCTCGT TCGGGGCGTC CCGGGAGCTG
201  GGAGCTGCGG GCGCCTGCGC GGGCTGCGCG TTTCACGGGG AGATCGGGGT
251  TGGCGTTGGC CGCAGATGCC TCTCGGTCCC TCCCTGTACT TACTGGTGAA
301  CAGCATTCAC CCAGAATGCC GATTTCATCT GGAAATACAG GAGGAAGAAA
351  CAAAATGTGC AGAGCTTCTG AGGTCTCAAA CAGAAAAACA CAAAGCCTGC
401  AGTGGCGTCT GGGACAACAT CACGTGCTGG CGGCCTGCTA ATGTGGAGA
451  GACCGTCACG GTGCCCTGCC CAAAAGTCTT CAGCAATTTT TACAGCAAAG
501  CAGGAAACAT AAGCAAAAAC TGTACGAGTG ATGGATGGTC AGAGACGTTC
551  CCAGATTTCG TCGATGCCTG TGGCTATAGC GACCCGGAGG ATGAGAGCAA
601  GATCACGTTT TATATTCTGG TGAAGGCCAT TTATACCCTG GGCTACAGTG
651  TCTCTCTGAT GTCTCTTGCA ACAGGAAGCA TAATTCTGTG CCTCTTCAGG
701  AAGCTGCACT GCACCAGGAA TTACATCCAC CTGAACCTGT TCCTGTCCTT
```

FIG.7A

```
 751  CATCCTGAGA GCCATCTCAG TGCTGGTCAA GGACGACGTT CTCTACTCCA
 801  GCTCTGGCAC GTTGCACTGC CCTGACCAGC CATCCTCCTG GGTGGGCTGC
 851  AAGCTGAGCC TGGTCTTCCT GCAGTACTGC ATCATGGCCA ACTTCTTCTG
 901  GCTGCTGGTG GAGGGGCTCT ACCTCCACAC CCTCCTGGTG GCCATGCTCC
 951  CCCCTAGAAG GTGCTTCCTG GCCTACCTCC TGATCGGATG GGGCCTCCCC
1001  ACCGTCTGCA TCGGTGCATG GACTGCGGCC AGGCTCTACT TAGAAGACAC
1051  CGGTTGCTGG GATACAAACG ACCACAGTGT GCCCTGGTGG GTCATACGAA
1101  TACCGATTTT AATTTCCATC ATCGTCAATT TTGTCCTTTT CATTAGTATT
1151  ATACGAATTT TGCTGCAGAA GTTAACATCC CCAGATGTCG GCGGCAACGA
1201  CCAGTCTCAG TACAAGAGGC TGGCCAAGTC CACGCTCCCT CTTATCCCGC
1251  TGTTCGGCGT CCACTACATG GTGTTTGCCG TGTTTCCCAT CAGCATCTCC
1301  TCCAAATACC AGATACTGTT TGAGCTGTGC CTCGGGTCGT TCCAGGCCT
1351  GGTGGTGGCC GTCCTCTACT GTTTCCTGAA CAGTGAGGTG CAGTGCCAGC
1401  TGAAGCGAAA ATGGCGAAGC CGGTGCCCGA CCCCGTCCGC GAGCCGGGAT
```

```
1451  TACAGGGTCT  GCGGTTCCTC  CTTCTCCCAC  AACGGCTCGG  AGGGCGCCCT
1501  GCAGTTCCAC  CGCGCGTCCC  GAGCCCAGTC  CTTCCTCCAA  ACGGAGACCT
1551  CGGTCATCTA  GCCCCACCCC  TGCCTGTCGG  ACGCGGCGGG  AGGCCCACGG
1601  TTCGGGGCTT  CTGCGGGGCT  GAGACGCCGG  CTTCCTCCTT  CCAGATGCCC
1651  GAGCACCGTG  TCGGGCTGGT  CAGCGGCGGTC  CTGACTCCGT  CAAGCTGGTT
1701  GTCCACTAAA  CCCCATACCT  GGAATTGGAG  TCGTGTTGTC  ATTGACTCAA
1751  CTTAAACTCC  AGCACCACGA  CCCTGCTGCT  ATCTCGCACC  TGAAACAAGC
1801  TAACATGACT  AACACCCTTA  ATTCCATCCA  CCCTCCTCTC  CCTAGGAGC
1851  CTGCGCCCGC  TAACCGGCTT  TTTCGCAAAT  GGGCCATTAT  CGAA
```

FIG.8A

```
R-2    1   MRTLLPPALLTCWLLAPVNSIHPECRFHLEIQEETKCAELLRSQTEKHK  50
                             ||||||||||||||||||||||||||||||
R-2B   1                   MPLGPSLYLLVNSIHPECRFHLEIQEETKCAELLRSQTEKHK  43

R-2    51  ACSGVWDNITCWRPANVGETVTVPCPKVFSNFYSKAGNISKNCTSDGWSE  100
           ||||||||||||||||||||||||||||||||||||||||||||||||||
R-2B   44  ACSGVWDNITCWRPANVGETVTVPCPKVFSNFYSKAGNISKNCTSDGWSE  93

R-2   101  TFPDFVDACGYSDPEDESKITFYILVKAIYTLGYSVSLMSLATGSIILCL  150
           ||||||||||||||||||||||||||||||||||||||||||||||||||
R-2B   94  TFPDFVDACGYSDPEDESKITFYILVKAIYTLGYSVSLMSLATGSIILCL  143

R-2   151  FRKLHCTRNYIHLNLFLSFILRAISVLVKDDVLYSSSGTLHCPDQPSSWV  200
           ||||||||||||||||||||||||||||||||||||||||||||||||||
R-2B  144  FRKLHCTRNYIHLNLFLSFILRAISVLVKDDVLYSSSGTLHCPDQPSSWV  193

R-2   201  GCKLSLVFLQYCIMANFFWLLVEGLYLHTLLVAMLPPRRCFLAYLLIGWG  250
           ||||||||||||||||||||||||||||||||||||||||||||||||||
R-2B  194  GCKLSLVFLQYCIMANFFWLLVEGLYLHTLLVAMLPPRRCFLAYLLIGWG  243
```

FIG.8B

```
251 LPTVCIGAWTAARLYLEDTGCWDTNDHSVPWWVIRIPILISIIVNFVLFI 300
    ||||||||||||||||||||||||||||||||||||||||||||||||||
244 LPTVCIGAWTAARLYLEDTGCWDTNDHSVPWWVIRIPILISIIVNFVLFI 293

301 SIIRILLLQLTSPDVGGNDQSQYKRLAKSTLLLIPLFGVHYMVFAVFPIS 350
    |||||||| |||||||||||||||||||||||||||||||||||||||||
294 SIIRILLQKLTSPDVGGNDQSQYKRLAKSTLLLIPLFGVHYMVFAVFPIS 343

351 ISSKYQILFELCLGSFQGLVVAVLYCFLNSEVQCELKRKWRRPCPDPAAS 400
    ||||||||||||||||||||||||||||||||||||||||||| | |||
344 ISSKYQILFELCLGSFQGLVVAVLYCFLNSEVQCELKRKWRSRCPTPSAS 393

401 RITELRSSSFSRNGSEGALQFLRESRAQSFLETETSVI 438
    ||| | |||| |||||||||| | |||||| ||||||
394 RDYRVCGSSFSHNGSEGALQFHRASRAQSFLQTETSVI 432
```

```
R2     1   ..........................GGGCCGGGACGGAGGGGCGGCCCCGC    28

R2B   51   CGCTGAGCTCCGGTCCCCGCCGGTTGCGACTCGGGTTGGGAGGCTGCCTG   100

29   GCTCGGGGCGCTCGGCTACAGCTGCGGGGCCCGAGGTCTCCGCGCAC....    75

101   CGCCCCTTCCCCGCGCCCCACCCGTCCGGGGTTTGCTGGAAACGGATCGTT   150

76   TCGCTCCCCGGCCCCATGCTGGAGGCGCCGAACCGGGACCTAGGA..CG    123

151   TCTTCCTGGACGCGTCAACGATGAGCTCGTTCGGGGCGTCCCGGAGCTG    200

124   GAGGCGGCGGCCCCCCGGCTGGGGCACGCTGAGCTCGGGATGCGG        173

201   GGAGCTGCGGGGCGCCTGCGCGGGCTGCGCGTTTCACGGGAGATCGGGGT   250

174   ACGCTGCTGCCTCCCGCGCTGCTGACCTGCTGCTGCTGCCCCGTGAA      223

251   TGGCGTTGGCCGCAGATGCCTCTCCGGTCCCCTGTACTTACTGGTGAA     300

224   CAGCATTCACCCAGAATGCCGATTTCATCTGGAAATACAGGAGGAAGAAA   273
           ||||||||||||||||||||||||||||||||||||||||||||||||||
     301   CAGCATTCACCCAGAATGCCGATTTCATCTGGAAATACAGGAGGAAGAAA   350

274   CAAAATGTGCAGAGCTTCTGAGGTCTCAAACAGAAAACACAAAGCCTGC    323
           ||||||||||||||||||||||||||||||||||||||||||||||||||
     351   CAAAATGTGCAGAGCTTCTGAGGTCTCAAACAGAAAAACACAAAGCCTGC   400
```

FIG.9A

```
R-2   324 AGTGGCGTCTGGGACAACATCACGTGCTGGCGGCCTGCTAATGTGGGAGA 373
          ||||||||||||||||||||||||||||||||||||||||||||||||||
R-2B  401 AGTGGGCGTCTGGGACAACATCACGTGCTGCTGGCGCGGCCTGCTAATGTGGGAGA 450

374 GACCGTCACGGTGCCCTGCCCAAAGTCTTCAGCAATTTTACAGCAAAG 423
          ||||||||||||||||||||||||||||||||||||||||||||||||
      451 GACCGTCACGGTGCCCTGCCCAAAGTCTTCAGCAATTTTACAGCAAAG 500

424 CAGGAAACATAAGCAAAAACTGTACGAGTGATGGTCAGAGACGTTC 473
          ||||||||||||||||||||||||||||||||||||||||||||||
      501 CAGGAAACATAAGCAAAAACTGTACGAGTGATGGTCAGAGACGTTC 550

474 CCAGATTTCGTCGATGCCTGTGGCTATAGCGACCCGGAGGATGAGAGCAA 523
          ||||||||||||||||||||||||||||||||||||||||||||||||||
      551 CCAGATTTCGTCGATGCCTGTGGCTATAGCGACCCGGAGGATGAGAGCAA 600

524 GATCACGTTTTATATTCTGGTGAAGGCCATTTATACCCTGGGCTACAGTG 573
          ||||||||||||||||||||||||||||||||||||||||||||||||||
      601 GATCACGTTTTATATTCTGGTGAAGGCCATTTATACCCTGGGCTACAGTG 650

574 TCTCTCTGATGTCTCTTGCAACAGGAAGCATAATTCTGTGCCTCTTCAGG 623
          ||||||||||||||||||||||||||||||||||||||||||||||||||
      651 TCTCTCTGATGTCTCTTGCAACAGGAAGCATAATTCTGTGCCTCTTCAGG 700

624 AAGCTGCACTGCACCAGGAATTACATCCACCTGAACCTGTCCTCCTT 673
          |||||||||||||||||||||||||||||||||||||||||||||||
      701 AAGCTGCACTGCACCAGGAATTACATCCACCTGAACCTGTCCTCCTT 750
```

FIG.9B

```
 674 CATCCTGAGAGCCATCTCAGTGCTGGTCAAGGACGACGTTCTCTACTCCA  723
     ||||||||||||||||||||||||||||||||||||||||||||||||||
 751 CATCCTGAGAGCCATCTCAGTGCTGGTCAAGGACGACGTTCTCTACTCCA  800

724 GCTCTGGCACGTTGCACTGCCCTGACCAGCCATCCTCCTGGGTGGGCTGC  773
     ||||||||||||||||||||||||||||||||||||||||||||||||||
 801 GCTCTGGCACGTTGCACTGCCCTGACCAGCCATCCTCCTGGGTGGGCTGC  850

774 AAGCTGAGCCCTGGTCTTCCTGCAGTACTGCATCATGGCCAACTTCTTCTG  823
     ||||||||||||||||||||||||||||||||||||||||||||||||||
 851 AAGCTGAGCCCTGGTCTTCCTGCAGTACTGCATCATGGCCAACTTCTTCTG  900

824 GCTGCTGGTGGAGGGGCTCTACCTCCACACCCTCCTGGTGGCCATGCTCC  873
     ||||||||||||||||||||||||||||||||||||||||||||||||||
 901 GCTGCTGGTGGAGGGGCTCTACCTCCACACCCTCCTGGTGGCCATGCTCC  950

874 CCCCTAGAAGGTGTGCTTCCTGGCCATGGACTGCCCAGGCTCTACTTAGAAGACAC  923
     ||||||||||||||||||||||||||||||||||||||||||||||||||
 951 CCCCTAGAAGGTGTGCTTCCTGGCCATGGACTGCCCAGGCTCTACTTAGAAGACAC  1000

924 ACCGTCTGCATCGGTGCATGGACTGCGCCACAGTGTGCCCTGGTGGGTCATACGAA  973
     ||||||||||||||||||||||||||||||||||||||||||||||||||
1001 ACCGTCTGCATCGGTGCATGGACTGCGCCACAGTGTGCCCTGGTGGGTCATACGAA  1050

974 CGGTTGCTGGGATACAAACGACCACAGTGTGCCCTGGTGGGTCATACGAA  1023
     ||||||||||||||||||||||||||||||||||||||||||||||||||
R-2B1051 CGGTTGCTGGGATACAAACGACCACAGTGTGCCCTGGTGGGTCATACGAA  1100
```

FIG. 9C

```
R-2    1024 TACCGATTTTAATTTCCATCATCGTCAATTTTGTCCTTTTCATTAGTATT 1073
             |||||||||||||||||||||||||||||||||||||||||||||||||
R-2B1101     TACCGATTTTAATTTCCATCATCGTCAATTTTGTCCTTTTCATTAGTATT 1150

1074 ATACGAATTTGCTGCAGAAGTTAACATCCCCAGATGTCGGCGGCAACGA 1123
             |||||||||||||||||||||||||||||||||||||||||||||||||
       1151 ATACGAATTTGCTGCAGAAGTTAACATCCCCAGATGTCGGCGGCAACGA 1200

1124 CCAGTCTCAGTACAAGAGAGGCTGGCCAAGTCCACGCTCCTGCTTATCCCGC 1173
             |||||||||||||||||||||||||||||||||||||||||||||||||
       1201 CCAGTCTCAGTACAAGAGAGGCTGGCCAAGTCCACGCTCCTGCTTATCCCGC 1250

1174 TGTTCGGCGTCCACTACATGGTGTTTGCCGTGTGTTTCCCATCAGCATCTCC 1223
             |||||||||||||||||||||||||||||||||||||||||||||||||
       1251 TGTTCGGCGTCCACTACATGGTGTTTGCCGTGTGTTTCCCATCAGCATCTCC 1300

1224 TCCAAATACCAGATACTGTTTGAGCTGTGCCTCGGGTCGTTCCAGGGCCT 1273
             |||||||||||||||||||||||||||||||||||||||||||||||||
       1301 TCCAAATACCAGATACTGTTTGAGCTGTGCCTCGGGTCGTTCCAGGGCCT 1350

1274 GGTGGTGGCCGTCCTCCTACTGTTCCCTGAACAGTGAGGTGCAGTGCGAGC 1323
             |||||||||||||||||||||||||||||||||||||||||||||||||
       1351 GGTGGTGGCCGTCCTCCTACTGTTCCCTGAACAGTGAGGTGCAGTGCGAGC 1400

1324 TGAAGCGAAAATGGCGAAGCCCGGTGCCCGTCCGCGAGCCGGGAT 1373
             |||||||||||||||||||||||||||||||||||||||||||||||||
       1401 TGAAGCGAAAATGGCGAAGCCCGGTGCCCGTCCGCGAGCCGGGAT 1450
```

FIG.9D

```
1374 TACAGGGTCTGCGGTTCCTCTCCCACAACGGCTCGGAGGGCGCCCT 1423
     ||||||||||||||||||||||||||||||||||||||||||||||
1451 TACAGGGTCTGCGGTTCCTCTCCCACAACGGCTCGGAGGGCGCCCT 1500

1424 GCAGTTCCACCGCGTCCCGAGCCCAGTCCTTCCTCCAAACGGAGACCT 1473
     ||||||||||||||||||||||||||||||||||||||||||||||||
1501 GCAGTTCCACCGCGTCCCGAGCCCAGTCCTTCCTCCAAACGGAGACCT 1550

1474 CGGTCATCTAGCCCCACCCCTGCCTGTCGGACGCGGGAGGCCCACGG 1523
     |||||||||||||||||||||||||||||||||||||||||||||||
1551 CGGTCATCTAGCCCCACCCCTGCCTGTCGGACGCGGGAGGCCCACGG 1600

1524 TTCGGGGCTTCTGCGCGGTGTCGGGCTGGTCAGCGCCGGCTTCCTCCTTCCAGATGCCC 1573
     ||||||||||||||||||||||||||||||||||||||||||||||||||||||||||
1601 TTCGGGGCTTCTGCGCGGTGTCGGGCTGGTCAGCGCCGGCTTCCTCCTTCCAGATGCCC 1650

1574 GAGCACCGTGTCGGGGCTGGTCAGCGCCGGTCCTGACTCCGTCAAGCTGTT 1623
     |||||||||||||||||||||||||||||||||||||||||||||||||||
1651 GAGCACCGTGTCGGGGCTGGTCAGCGCCGGTCCTGACTCCGTCAAGCTGTT 1700

1624 GTCCACTAAAACCCATACCTGGAATTGGAGTCGTGTTGTCATTGACTCAA 1673
     ||||||||||||||||||||||||||||||||||||||||||||||||||
1701 GTCCACTAAAACCCATACCTGGAATTGGAGTCGTGTTGTCATTGACTCAA 1750

R-2    1674 CTTAAACTCCAGCACCACGACCCTGCTGTATCTCGCACCTGAAACAAGC 1723
            ||||||||||||||||||||||||||||||||||||||||||||||||
R-2B   1751 CTTAAACTCCAGCACCACGACCCTGCTGTATCTCGCACCTGAAACAAGC 1800
```

```
1724 TAACATGACTAACACCCTTAATTCCATCCACCCTCCTCCCTAGGAGGC 1773
     ||||||||||||||||||||||||||||||||||||||||||||||||
1801 TAACATGACTAACACCCTTAATTCCATCCACCCTCCTCCCTAGGAGGC 1850

1774 CTGCGCCCCGCTAACCGGCTTTTTCGCAAATGGGCCATTATCGAA 1817
     |||||||||||||||||||||||||||||||||||||||||||||
1851 CTGCGCCCCGCTAACCGGCTTTTTCGCAAATGGGCCATTATCGAA 1894
```

5,882,899

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:

(A) LENGTH: 438 amino acids
(B) TYPE: amino acid
(C) STRANDEDNESS: single
(D) TOPOLOGY: linear (ii) MOLECULE TYPE: protein
(A) DESCRIPTION: Human PACAP/VIP R-2

(iii) HYPOTHETICAL: NO (xi) SEQUENCE DESCRIPTION: SEQ ID NO:1:

```
Met Arg Thr Leu Leu Pro Pro Ala Leu Leu Thr Cys Trp Leu Leu Ala
1               5                   10                  15

Pro Val Asn Ser Ile His Pro Glu Cys Arg Phe His Leu Glu Ile Gln
            20                  25                  30

Glu Glu Glu Thr Lys Cys Ala Glu Leu Leu Arg Ser Gln Thr Glu Lys
        35                  40                  45

His Lys Ala Cys Ser Gly Val Trp Asp Asn Ile Thr Cys Trp Arg Pro
    50                  55                  60

Ala Asn Val Gly Glu Thr Val Thr Val Pro Cys Pro Lys Val Phe Ser
65                  70                  75                  80

Asn Phe Tyr Ser Lys Ala Gly Asn Ile Ser Lys Asn Cys Thr Ser Asp
                85                  90                  95

Gly Trp Ser Glu Thr Phe Pro Asp Phe Val Asp Ala Cys Gly Tyr Ser
            100                 105                 110

Asp Pro Glu Asp Glu Ser Lys Ile Thr Phe Tyr Ile Leu Val Lys Ala
            115                 120                 125

Ile Tyr Thr Leu Gly Tyr Ser Val Ser Leu Met Ser Leu Ala Thr Gly
    130                 135                 140

Ser Ile Ile Leu Cys Leu Phe Arg Lys Leu His Cys Thr Arg Asn Tyr
145                 150                 155                 160

Ile His Leu Asn Leu Phe Leu Ser Phe Ile Leu Arg Ala Ile Ser Val
                165                 170                 175

Leu Val Lys Asp Asp Val Leu Tyr Ser Ser Gly Thr Leu His Cys
            180                 185                 190

Pro Asp Gln Pro Ser Ser Trp Val Gly Cys Lys Leu Ser Leu Val Phe
        195                 200                 205

Leu Gln Tyr Cys Ile Met Ala Asn Phe Phe Trp Leu Leu Val Glu Gly
    210                 215                 220

Leu Tyr Leu His Thr Leu Leu Val Ala Met Leu Pro Pro Arg Arg Cys
225                 230                 235                 240

Phe Leu Ala Tyr Leu Leu Ile Gly Trp Gly Leu Pro Thr Val Cys Ile
                245                 250                 255

Gly Ala Trp Thr Ala Ala Arg Leu Tyr Leu Glu Asp Thr Gly Cys Trp
            260                 265                 270

Asp Thr Asn Asp His Ser Val Pro Trp Trp Val Ile Arg Ile Pro Ile
        275                 280                 285

Leu Ile Ser Ile Ile Val Asn Phe Val Leu Phe Ile Ser Ile Ile Arg
    290                 295                 300

Ile Leu Leu Gln Lys Leu Thr Ser Pro Asp Val Gly Gly Asn Asp Gln
305                 310                 315                 320

Ser Gln Tyr Lys Arg Leu Ala Lys Ser Thr Leu Leu Leu Ile Pro Leu
                325                 330                 335

Phe Gly Val His Tyr Met Val Phe Ala Val Phe Pro Ile Ser Ile Ser
            340                 345                 350

Ser Lys Tyr Gln Ile Leu Phe Glu Leu Cys Leu Gly Ser Phe Gln Gly
        355                 360                 365
```

|     |     |     |     |     |     |     |     |     |     |     |     |     |     |     |
| --- | --- | --- | --- | --- | --- | --- | --- | --- | --- | --- | --- | --- | --- | --- |
| Leu | Val | Val | Ala | Val | Leu | Tyr | Cys | Phe | Leu | Asn | Ser | Glu | Val | Gln | Cys |
| 370 |     |     |     |     | 375 |     |     |     |     | 380 |     |     |     |     |     |
| Glu | Leu | Lys | Arg | Lys | Trp | Arg | Ser | Arg | Cys | Pro | Thr | Pro | Ser | Ala | Ser |
| 385 |     |     |     | 390 |     |     |     |     | 395 |     |     |     |     |     | 400 |
| Arg | Asp | Tyr | Arg | Val | Cys | Gly | Ser | Ser | Phe | Ser | His | Asn | Gly | Ser | Glu |
|     |     |     |     | 405 |     |     |     |     | 410 |     |     |     |     | 415 |     |
| Gly | Ala | Leu | Gln | Phe | His | Arg | Ala | Ser | Arg | Ala | Gln | Ser | Phe | Leu | Gln |
|     |     |     | 420 |     |     |     |     | 425 |     |     |     |     | 430 |     |     |
| Thr | Glu | Thr | Ser | Val | Ile |
|     |     | 435 |     |     |     |

( 2 ) INFORMATION FOR SEQ ID NO:2:

( i ) SEQUENCE CHARACTERISTICS:
    ( A ) LENGTH: 437 amino acids
    ( B ) TYPE: amino acid
    ( C ) STRANDEDNESS: single
    ( D ) TOPOLOGY: linear ( i i ) MOLECULE TYPE: protein
    ( A ) DESCRIPTION: RPACAP-3/RVIP-2

( i i i ) HYPOTHETICAL: NO ( x i ) SEQUENCE DESCRIPTION: SEQ ID NO:2:

| Met | Arg | Ala | Ser | Val | Val | Leu | Thr | Cys | Tyr | Cys | Trp | Leu | Leu | Val | Arg |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Val | Ser | Ser | Ile | His | Pro | Glu | Cys | Arg | Phe | His | Leu | Glu | Ile | Gln | Glu |
|     |     |     | 20 |     |     |     |     | 25 |     |     |     |     | 30 |     |     |
| Glu | Glu | Thr | Lys | Cys | Ala | Glu | Leu | Leu | Ser | Ser | Gln | Thr | Glu | Asn | Gln |
|     |     | 35 |     |     |     |     | 40 |     |     |     |     | 45 |     |     |     |
| Arg | Ala | Cys | Ser | Gly | Val | Trp | Asp | Asn | Ile | Thr | Cys | Trp | Arg | Pro | Ala |
|     | 50 |     |     |     |     | 55 |     |     |     |     | 60 |     |     |     |     |
| Asp | Val | Gly | Glu | Thr | Val | Thr | Val | Pro | Cys | Pro | Lys | Val | Phe | Ser | Asn |
| 65 |     |     |     |     | 70 |     |     |     |     | 75 |     |     |     |     | 80 |
| Phe | Tyr | Ser | Arg | Pro | Gly | Asn | Ile | Ser | Lys | Asn | Cys | Thr | Ser | Asp | Gly |
|     |     |     |     | 85 |     |     |     |     | 90 |     |     |     |     | 95 |     |
| Trp | Ser | Glu | Thr | Phe | Pro | Asp | Phe | Ile | Asp | Ala | Cys | Gly | Tyr | Asn | Asp |
|     |     |     | 100 |     |     |     |     | 105 |     |     |     |     | 110 |     |     |
| Pro | Glu | Asp | Glu | Ser | Lys | Ile | Ser | Phe | Tyr | Ile | Leu | Val | Lys | Ala | Ile |
|     |     | 115 |     |     |     |     | 120 |     |     |     |     | 125 |     |     |     |
| Tyr | Thr | Leu | Gly | Tyr | Ser | Val | Ser | Leu | Met | Ser | Leu | Thr | Thr | Gly | Ser |
|     | 130 |     |     |     |     | 135 |     |     |     |     | 140 |     |     |     |     |
| Ile | Ile | Ile | Cys | Leu | Phe | Arg | Lys | Leu | His | Cys | Thr | Arg | Asn | Tyr | Ile |
| 145 |     |     |     |     | 150 |     |     |     |     | 155 |     |     |     |     | 160 |
| His | Leu | Asn | Leu | Phe | Leu | Ser | Phe | Met | Leu | Arg | Ala | Ile | Ser | Val | Leu |
|     |     |     |     | 165 |     |     |     |     | 170 |     |     |     |     | 175 |     |
| Val | Lys | Asp | Ser | Val | Leu | Tyr | Ser | Ser | Ser | Gly | Leu | Leu | Arg | Cys | His |
|     |     |     | 180 |     |     |     |     | 185 |     |     |     |     | 190 |     |     |
| Asp | Gln | Pro | Ala | Ser | Trp | Val | Gly | Cys | Lys | Leu | Ser | Leu | Val | Phe | Phe |
|     |     | 195 |     |     |     |     | 200 |     |     |     |     | 205 |     |     |     |
| Gln | Tyr | Cys | Ile | Met | Ala | Asn | Phe | Tyr | Trp | Leu | Leu | Val | Glu | Gly | Leu |
|     | 210 |     |     |     |     | 215 |     |     |     |     | 220 |     |     |     |     |
| Tyr | Leu | His | Thr | Leu | Leu | Val | Ala | Ile | Leu | Pro | Pro | Ser | Arg | Cys | Phe |
| 225 |     |     |     |     | 230 |     |     |     |     | 235 |     |     |     |     | 240 |
| Leu | Ala | Tyr | Leu | Leu | Ile | Gly | Trp | Gly | Ile | Pro | Ser | Val | Cys | Ile | Gly |
|     |     |     |     | 245 |     |     |     |     | 250 |     |     |     |     | 255 |     |

```
Ala Trp Thr Ala Thr Arg Leu Ser Leu Glu Asp Thr Gly Cys Trp Asp
            260                 265                 270

Thr Asn Asp His Ser Ile Pro Trp Trp Val Ile Arg Met Pro Ile Leu
        275             280                 285

Ile Ser Ile Val Val Asn Phe Ala Leu Phe Ile Ser Ile Val Arg Ile
    290             295                 300

Leu Leu Gln Lys Leu Thr Ser Pro Asp Val Gly Gly Asn Asp Gln Ser
305                 310                 315                 320

Gln Tyr Lys Arg Leu Ala Lys Ser Thr Leu Leu Ile Pro Leu Phe
            325             330                 335

Gly Val His Tyr Met Val Phe Ala Ala Phe Pro Ile Gly Ile Ser Ser
            340             345                 350

Thr Tyr Gln Ile Leu Phe Glu Leu Cys Val Gly Ser Phe Gln Gly Leu
        355             360                 365

Val Val Ala Val Leu Tyr Cys Phe Leu Asn Ser Glu Val Gln Cys Glu
        370             375                 380

Leu Lys Arg Arg Trp Arg Gly Leu Cys Leu Thr Gln Ala Gly Ser Arg
385                 390                 395                 400

Asp Tyr Arg Leu His Ser Trp Ser Met Ser Arg Asn Gly Ser Glu Ser
            405                 410                 415

Ala Leu Gln Ile His Arg Gly Ser Arg Thr Gln Ser Phe Leu Gln Ser
            420                 425                 430

Glu Thr Ser Val Ile
            435
```

(2) INFORMATION FOR SEQ ID NO:3:

(i) SEQUENCE CHARACTERISTICS:
        (A) LENGTH: 1817 base pairs
        (B) TYPE: nucleic acid
        (C) STRANDEDNESS: double
        (D) TOPOLOGY: linear (ii) MOLECULE TYPE: cDNA
        (A) DESCRIPTION: Human PACAP/VIP R-2

(iii) HYPOTHETICAL: NO (iv) ANTI-SENSE: NO (xi) SEQUENCE DESCRIPTION: SEQ ID NO:3:

```
GGGCCGGGAC GGAGGGGGCG GCCCCCGCGC TCGGGGCGCT CGGCTACAGC TGCGGGGCCC      60
GAGGTCTCCG CGCACTCGCT CCCGGCCCAT GCTGGAGGCG CGGAACCGCG GGGACCTAGG     120
ACGGAGGCGG CGGGCGCTGG GGCGGCCCCC GGCACGCTGA GCTCGGGATG CGGACGCTGC     180
TGCCTCCCGC GCTGCTGACC TGCTGGCTGC TCGCCCCCGT GAACAGCATT CACCCAGAAT     240
GCCGATTTCA TCTGGAAATA CAGGAGGAAG AAACAAAATG TGCAGAGCTT CTGAGGTCTC     300
AAACAGAAAA ACACAAAGCC TGCAGTGGCG TCTGGGACAA CATCACGTGC TGGCGGCCTG     360
CTAATGTGGG AGAGACCGTC ACGGTGCCCT GCCCAAAAGT CTTCAGCAAT TTTTACAGCA     420
AAGCAGGAAA CATAAGCAAA AACTGTACGA GTGATGGATG GTCAGAGACG TTCCCAGATT     480
TCGTCGATGC CTGTGGCTAT AGCGACCCGG AGGATGAGAG CAAGATCACG TTTTATATTC     540
TGGTGAAGGC CATTTATACC CTGGGCTACA GTGTCTCTCT GATGTCTCTT GCAACAGGAA     600
GCATAATTCT GTGCCTCTTC AGGAAGCTGC ACTGCACCAG GAATTACATC CACCTGAACC     660
TGTTCCTGTC CTTCATCCTG AGAGCCATCT CAGTGCTGGT CAAGGACGAC GTTCTCTACT     720
CCAGCTCTGG CACGTTGCAC TGCCCTGACC AGCCATCCTC CTGGGTGGGC TGCAAGCTGA     780
```

| | | | | | | |
|---|---|---|---|---|---|---|
| GCCTGGTCTT | CCTGCAGTAC | TGCATCATGG | CCAACTTCTT | CTGGCTGCTG | GTGGAGGGGC | 840 |
| TCTACCTCCA | CACCCTCCTG | GTGGCCATGC | TCCCCCCTAG | AAGGTGCTTC | CTGGCCTACC | 900 |
| TCCTGATCGG | ATGGGGCCTC | CCCACCGTCT | GCATCGGTGC | ATGGACTGCG | GCCAGGCTCT | 960 |
| ACTTAGAAGA | CACCGGTTGC | TGGGATACAA | ACGACCACAG | TGTGCCCTGG | TGGGTCATAC | 1020 |
| GAATACCGAT | TTTAATTTCC | ATCATCGTCA | ATTTGTCCT | TTTCATTAGT | ATTATACGAA | 1080 |
| TTTTGCTGCA | GAAGTTAACA | TCCCCAGATG | TCGGCGGCAA | CGACCAGTCT | CAGTACAAGA | 1140 |
| GGCTGGCCAA | GTCCACGCTC | CTGCTTATCC | CGCTGTTCGG | CGTCCACTAC | ATGGTGTTTG | 1200 |
| CCGTGTTTCC | CATCAGCATC | TCCTCCAAAT | ACCAGATACT | GTTTGAGCTG | TGCCTCGGGT | 1260 |
| CGTTCCAGGG | CCTGGTGGTG | GCCGTCCTCT | ACTGTTTCCT | GAACAGTGAG | GTGCAGTGCG | 1320 |
| AGCTGAAGCG | AAAATGGCGA | AGCCGGTGCC | CGACCCCGTC | CGCGAGCCGG | GATTACAGGG | 1380 |
| TCTGCGGTTC | CTCCTTCTCC | CACAACGGCT | CGGAGGGCGC | CCTGCAGTTC | CACCGCGCGT | 1440 |
| CCCGAGCCCA | GTCCTTCCTC | CAAACGGAGA | CCTCGGTCAT | CTAGCCCCAC | CCCTGCCTGT | 1500 |
| CGGACGCGGC | GGGAGGCCCA | CGGTTCGGGG | CTTCTGCGGG | GCTGAGACGC | CGGCTTCCTC | 1560 |
| CTTCCAGATG | CCCGAGCACC | GTGTCGGGCT | GGTCAGCGCG | GTCCTGACTC | CGTCAAGCTG | 1620 |
| GTTGTCCACT | AAACCCCATA | CCTGGAATTG | GAGTCGTGTT | GTCATTGACT | CAACTTAAAC | 1680 |
| TCCAGCACCA | CGACCCTGCT | GCTATCTCGC | ACCTGAAACA | AGCTAACATG | ACTAACACCC | 1740 |
| TTAATTCCAT | CCACCCTCCT | CTCCCTAGGA | GGCCTGCGCC | CGCTAACCGG | CTTTTTCGCA | 1800 |
| AATGGGCCAT | TATCGAA | | | | | 1817 |

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA
        (A) DESCRIPTION: Primer for amplification of the cDNA fragment of PACAP-Type 1 receptor (iii) HYPOTHETICAL: NO (iv) ANTI-SENSE: NO (xi) SEQUENCE DESCRIPTION: SEQ ID NO:4:

ATAGTACTGG TCAGCTGCCC TGAGCTC        27

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA
        (A) DESCRIPTION: Primer for amplification of the cDNA fragment of PACAP-Type 1 receptor (iii) HYPOTHETICAL: NO (iv) ANTI-SENSE: YES (xi) SEQUENCE DESCRIPTION: SEQ ID NO:5:

CAGTCTCAGA TTCATATTCA TC        22

(2) INFORMATION FOR SEQ ID NO:6:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA
  ( A ) DESCRIPTION: Primer for amplification of the cDNA fragment of PACAP/VIP R1

( i i i ) HYPOTHETICAL: NO ( i v ) ANTI-SENSE: NO ( x i ) SEQUENCE DESCRIPTION: SEQ ID NO:6:

| | | |
|---|---|---|
| CAATAGGCTG CAGCAAGATG T | | 21 |

( 2 ) INFORMATION FOR SEQ ID NO:7:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA
  ( A ) DESCRIPTION: Primer for amplification of the cDNA fragment of PACAP/VIP R1

( i i i ) HYPOTHETICAL: NO ( i v ) ANTI-SENSE: YES ( x i ) SEQUENCE DESCRIPTION: SEQ ID NO:7:

| | | |
|---|---|---|
| ACAGAACCGT AGAACATGGT C | | 21 |

( 2 ) INFORMATION FOR SEQ ID NO:8:

( i ) SEQUENCE CHARACTERISTICS:
  ( A ) LENGTH: 1894 base pairs
  ( B ) TYPE: nucleic acid
  ( C ) STRANDEDNESS: double
  ( D ) TOPOLOGY: linear ( i i ) MOLECULE TYPE: cDNA
  ( A ) DESCRIPTION: Human PACAP/VIP R- 2B (full length)

( i i i ) HYPOTHETICAL: NO ( i v ) ANTI-SENSE: NO ( x i ) SEQUENCE DESCRIPTION: SEQ ID NO:8:

| | | | | | | |
|---|---|---|---|---|---|---|
| GGGGAGCGGG | GTCGCCCGGG | GTCCGGAGCT | TCCTCCCGGA | GAGCGTGAAG | CGCTGAGCTC | 60 |
| CGGTCCCGCC | GGTTGCGGAC | TCGGGTTGGG | AGGCTGCCTG | CGCCCTTCCC | CGCGCCCCAC | 120 |
| CGTCCGGGGT | TTGCTGGAAA | CGGGATCGTT | TCTTCCTGGA | CGCGTCAACG | ATGAGCTCGT | 180 |
| TCGGGGCGTC | CCGGGAGCTG | GGAGCTGCGG | GCGCCTGCGC | GGGCTGCGCG | TTTCACGGGG | 240 |
| AGATCGGGGT | TGGCGTTGGC | CGCAGATGCC | TCTCGGTCCC | TCCCTGTACT | TACTGGTGAA | 300 |
| CAGCATTCAC | CCAGAATGCC | GATTTCATCT | GGAAATACAG | GAGGAAGAAA | CAAAATGTGC | 360 |
| AGAGCTTCTG | AGGTCTCAAA | CAGAAAAACA | CAAAGCCTGC | AGTGGCGTCT | GGGACAACAT | 420 |
| CACGTGCTGG | CGGCCTGCTA | ATGTGGGAGA | GACCGTCACG | GTGCCCTGCC | CAAAAGTCTT | 480 |
| CAGCAATTTT | TACAGCAAAG | CAGGAAACAT | AAGCAAAAAC | TGTACGAGTG | ATGGATGGTC | 540 |
| AGAGACGTTC | CCAGATTTCG | TCGATGCCTG | TGGCTATAGC | GACCCGGAGG | ATGAGAGCAA | 600 |
| GATCACGTTT | TATATTCTGG | TGAAGGCCAT | TTATACCCTG | GGCTACAGTG | TCTCTCTGAT | 660 |

| | | | | | |
|---|---|---|---|---|---|
| GTCTCTTGCA | ACAGGAAGCA | TAATTCTGTG | CCTCTTCAGG | AAGCTGCACT | GCACCAGGAA | 720 |
| TTACATCCAC | CTGAACCTGT | TCCTGTCCTT | CATCCTGAGA | GCCATCTCAG | TGCTGGTCAA | 780 |
| GGACGACGTT | CTCTACTCCA | GCTCTGGCAC | GTTGCACTGC | CCTGACCAGC | CATCCTCCTG | 840 |
| GGTGGGCTGC | AAGCTGAGCC | TGGTCTTCCT | GCAGTACTGC | ATCATGGCCA | ACTTCTTCTG | 900 |
| GCTGCTGGTG | GAGGGGCTCT | ACCTCCACAC | CCTCCTGGTG | GCCATGCTCC | CCCCTAGAAG | 960 |
| GTGCTTCCTG | GCCTACCTCC | TGATCGGATG | GGGCCTCCCC | ACCGTCTGCA | TCGGTGCATG | 1020 |
| GACTGCGGCC | AGGCTCTACT | TAGAAGACAC | CGGTTGCTGG | GATACAAACG | ACCACAGTGT | 1080 |
| GCCCTGGTGG | GTCATACGAA | TACCGATTTT | AATTTCCATC | ATCGTCAATT | TTGTCCTTTT | 1140 |
| CATTAGTATT | ATACGAATTT | TGCTGCAGAA | GTTAACATCC | CAGATGTCG | GCGGCAACGA | 1200 |
| CCAGTCTCAG | TACAAGAGGC | TGGCCAAGTC | CACGCTCCTG | CTTATCCCGC | TGTTCGGCGT | 1260 |
| CCACTACATG | GTGTTTGCCG | TGTTTCCCAT | CAGCATCTCC | TCCAAATACC | AGATACTGTT | 1320 |
| TGAGCTGTGC | CTCGGGTCGT | TCCAGGGCCT | GGTGGTGGCC | GTCCTCTACT | GTTTCCTGAA | 1380 |
| CAGTGAGGTG | CAGTGCGAGC | TGAAGCGAAA | ATGGCGAAGC | CGGTGCCCGA | CCCCGTCCGC | 1440 |
| GAGCCGGGAT | TACAGGGTCT | GCGGTTCCTC | CTTCTCCCAC | AACGGCTCGG | AGGGCGCCCT | 1500 |
| GCAGTTCCAC | CGCGCGTCCC | GAGCCCAGTC | CTTCCTCCAA | ACGGAGACCT | CGGTCATCTA | 1560 |
| GCCCCACCCC | TGCCTGTCGG | ACGCGGCGGG | AGGCCCACGG | TTCGGGGCTT | CTGCGGGGCT | 1620 |
| GAGACGCCGG | CTTCCTCCTT | CCAGATGCCC | GAGCACCGTG | TCGGGCTGGT | CAGCGCGGTC | 1680 |
| CTGACTCCGT | CAAGCTGGTT | GTCCACTAAA | CCCCATACCT | GGAATTGGAG | TCGTGTTGTC | 1740 |
| ATTGACTCAA | CTTAAACTCC | AGCACCACGA | CCCTGCTGCT | ATCTCGCACC | TGAAACAAGC | 1800 |
| TAACATGACT | AACACCCTTA | ATTCCATCCA | CCCTCCTCTC | CCTAGGAGGC | CTGCGCCCGC | 1860 |
| TAACCGGCTT | TTTCGCAAAT | GGGCCATTAT | CGAA | | | 1894 |

(2) INFORMATION FOR SEQ ID NO:9:

(i) SEQUENCE CHARACTERISTICS:
        (A) LENGTH: 431 amino acids
        (B) TYPE: amino acid
        (C) STRANDEDNESS: single
        (D) TOPOLOGY: linear (ii) MOLECULE TYPE: protein
        (A) DESCRIPTION: Human PACAP/VIP R- 2B (iii) HYPOTHETICAL: NO (xi) SEQUENCE DESCRIPTION: SEQ ID NO:9:

```
Met Pro Leu Gly Pro Ser Leu Tyr Leu Leu Val Asn Ser Ile His Pro
 1               5                  10                  15

Glu Cys Arg Phe His Leu Glu Ile Gln Glu Glu Thr Lys Cys Ala
                 20                  25                  30

Glu Leu Leu Arg Ser Gln Thr Glu Lys His Lys Ala Cys Ser Gly Val
             35                  40                  45

Trp Asp Asn Ile Thr Cys Trp Arg Pro Ala Asn Val Gly Glu Thr Val
         50                  55                  60

Thr Val Pro Cys Pro Lys Val Phe Ser Asn Phe Tyr Ser Lys Ala Gly
 65                  70                  75                  80

Asn Ile Ser Lys Asn Cys Thr Ser Asp Gly Trp Ser Glu Thr Phe Pro
                 85                  90                  95

Asp Phe Val Asp Ala Cys Gly Tyr Ser Asp Pro Glu Asp Glu Ser Lys
                100                 105                 110

Ile Thr Phe Tyr Ile Leu Val Lys Ala Ile Tyr Thr Leu Gly Tyr Ser
```

|     |     |     |     |     | 115 |     |     |     | 120 |     |     |     | 125 |     |
|-----|-----|-----|-----|-----|-----|-----|-----|-----|-----|-----|-----|-----|-----|-----|

Val Ser Leu Met Ser Leu Ala Thr Gly Ser Ile Ile Leu Cys Leu Phe
130                     135                 140

Arg Lys Leu His Cys Thr Arg Asn Tyr Ile His Leu Asn Leu Phe Leu
145                 150                 155                         160

Ser Phe Ile Leu Arg Ala Ile Ser Val Leu Val Lys Asp Asp Val Leu
                    165                 170                 175

Tyr Ser Ser Ser Gly Thr Leu His Cys Pro Asp Gln Pro Ser Ser Trp
            180                 185                 190

Val Gly Cys Lys Leu Ser Leu Val Phe Leu Gln Tyr Cys Ile Met Ala
        195                 200                 205

Asn Phe Phe Trp Leu Leu Val Glu Gly Leu Tyr Leu His Thr Leu Leu
    210                 215                 220

Val Ala Met Leu Pro Pro Arg Arg Cys Phe Leu Ala Tyr Leu Leu Ile
225                 230                 235                         240

Gly Trp Gly Leu Pro Thr Val Cys Ile Gly Ala Trp Thr Ala Ala Arg
                245                 250                 255

Leu Tyr Leu Glu Asp Thr Gly Cys Trp Asp Thr Asn Asp His Ser Val
            260                 265                 270

Pro Trp Trp Val Ile Arg Ile Pro Ile Leu Ile Ser Ile Ile Val Asn
        275                 280                 285

Phe Val Leu Phe Ile Ser Ile Ile Arg Ile Leu Leu Gln Lys Leu Thr
    290                 295                 300

Ser Pro Asp Val Gly Gly Asn Asp Gln Ser Gln Tyr Lys Arg Leu Ala
305                 310                 315                         320

Lys Ser Thr Leu Leu Leu Ile Pro Leu Phe Gly Val His Tyr Met Val
                325                 330                 335

Phe Ala Val Phe Pro Ile Ser Ile Ser Ser Lys Tyr Gln Ile Leu Phe
            340                 345                 350

Glu Leu Cys Leu Gly Ser Phe Gln Gly Leu Val Val Ala Val Leu Tyr
        355                 360                 365

Cys Phe Leu Asn Ser Glu Val Gln Cys Glu Leu Lys Arg Lys Trp Arg
    370                 375                 380

Ser Arg Cys Pro Thr Pro Ser Ala Ser Arg Asp Tyr Arg Val Cys Gly
385                 390                 395                         400

Ser Ser Phe Ser His Asn Gly Ser Glu Gly Ala Leu Gln Phe His Arg
                405                 410                 415

Ala Ser Arg Ala Gln Ser Phe Leu Gln Thr Glu Thr Ser Val Ile
            420                 425                 430

( 2 ) INFORMATION FOR SEQ ID NO:10:

( i ) SEQUENCE CHARACTERISTICS:
        ( A ) LENGTH: 1844 base pairs
        ( B ) TYPE: nucleic acid
        ( C ) STRANDEDNESS: double
        ( D ) TOPOLOGY: linear ( i i ) MOLECULE TYPE: cDNA
        ( A ) DESCRIPTION: Human PACAP/VIP R- 2B (Base 51 to end)

( i i i ) HYPOTHETICAL: NO ( i v ) ANTI-SENSE: NO ( x i ) SEQUENCE DESCRIPTION: SEQ ID NO:10:

CGCTGAGCTC CGGTCCCGCC GGTTGCGGAC TCGGGTTGGG AGGCTGCCTG CGCCCTTCCC     60

CGCGCCCCAC CGTCCGGGGT TTGCTGGAAA CGGGATCGTT TCTTCCTGGA CGCGTCAACG    120

-continued

| | | | | | | |
|---|---|---|---|---|---|---|
| ATGAGCTCGT | TCGGGGCGTC | CCGGGAGCTG | GGAGCTGCGG | GCGCCTGCGC | GGGCTGCGCG | 180 |
| TTTCACGGGG | AGATCGGGGT | TGGCGTTGGC | CGCAGATGCC | TCTCGGTCCC | TCCCTGTACT | 240 |
| TACTGGTGAA | CAGCATTCAC | CCAGAATGCC | GATTTCATCT | GGAAATACAG | GAGGAAGAAA | 300 |
| CAAAATGTGC | AGAGCTTCTG | AGGTCTCAAA | CAGAAAAACA | CAAAGCCTGC | AGTGGCGTCT | 360 |
| GGGACAACAT | CACGTGCTGG | CGGCCTGCTA | ATGTGGGAGA | GACCGTCACG | GTGCCCTGCC | 420 |
| CAAAGTCTT | CAGCAATTTT | TACAGCAAAG | CAGGAAACAT | AAGCAAAAAC | TGTACGAGTG | 480 |
| ATGGATGGTC | AGAGACGTTC | CCAGATTTCG | TCGATGCCTG | TGGCTATAGC | GACCCGGAGG | 540 |
| ATGAGAGCAA | GATCACGTTT | TATATTCTGG | TGAAGGCCAT | TTATACCCTG | GGCTACAGTG | 600 |
| TCTCTCTGAT | GTCTCTTGCA | ACAGGAAGCA | TAATTCTGTG | CCTCTTCAGG | AAGCTGCACT | 660 |
| GCACCAGGAA | TTACATCCAC | CTGAACCTGT | TCCTGTCCTT | CATCCTGAGA | GCCATCTCAG | 720 |
| TGCTGGTCAA | GGACGACGTT | CTCTACTCCA | GCTCTGGCAC | GTTGCACTGC | CCTGACCAGC | 780 |
| CATCCTCCTG | GGTGGGCTGC | AAGCTGAGCC | TGGTCTTCCT | GCAGTACTGC | ATCATGGCCA | 840 |
| ACTTCTTCTG | GCTGCTGGTG | GAGGGGCTCT | ACCTCCACAC | CCTCCTGGTG | GCCATGCTCC | 900 |
| CCCCTAGAAG | GTGCTTCCTG | GCCTACCTCC | TGATCGGATG | GGGCCTCCCC | ACCGTCTGCA | 960 |
| TCGGTGCATG | GACTGCGGCC | AGGCTCTACT | TAGAAGACAC | CGGTTGCTGG | GATACAAACG | 1020 |
| ACCACAGTGT | GCCCTGGTGG | GTCATACGAA | TACCGATTTT | AATTTCCATC | ATCGTCAATT | 1080 |
| TTGTCCTTTT | CATTAGTATT | ATACGAATTT | TGCTGCAGAA | GTTAACATCC | CCAGATGTCG | 1140 |
| GCGGCAACGA | CCAGTCTCAG | TACAAGAGGC | TGGCCAAGTC | CACGCTCCTG | CTTATCCCGC | 1200 |
| TGTTCGGCGT | CCACTACATG | GTGTTTGCCG | TGTTTCCCAT | CAGCATCTCC | TCCAAATACC | 1260 |
| AGATACTGTT | TGAGCTGTGC | CTCGGGTCGT | TCCAGGGCCT | GGTGGTGGCC | GTCCTCTACT | 1320 |
| GTTTCCTGAA | CAGTGAGGTG | CAGTGCGAGC | TGAAGCGAAA | ATGGCGAAGC | CGGTGCCCGA | 1380 |
| CCCCGTCCGC | GAGCCGGGAT | TACAGGGTCT | GCGGTTCCTC | CTTCTCCCAC | AACGGCTCGG | 1440 |
| AGGGCGCCCT | GCAGTTCCAC | CGCGCGTCCC | GAGCCCAGTC | CTTCCTCCAA | ACGGAGACCT | 1500 |
| CGGTCATCTA | GCCCCACCCC | TGCCTGTCGG | ACGCGGCGGG | AGGCCCACGG | TTCGGGGCTT | 1560 |
| CTGCGGGGCT | GAGACGCCGG | CTTCCTCCTT | CCAGATGCCC | GAGCACCGTG | TCGGGCTGGT | 1620 |
| CAGCGCGGTC | CTGACTCCGT | CAAGCTGGTT | GTCCACTAAA | CCCCATACCT | GGAATTGGAG | 1680 |
| TCGTGTTGTC | ATTGACTCAA | CTTAAACTCC | AGCACCACGA | CCCTGCTGCT | ATCTCGCACC | 1740 |
| TGAAACAAGC | TAACATGACT | AACACCCTTA | ATTCCATCCA | CCCTCCTCTC | CCTAGGAGGC | 1800 |
| CTGCGCCCGC | TAACCGGCTT | TTTCGCAAAT | GGGCCATTAT | CGAA | | 1844 |

RECEPTOR FOR PEPTIDE HORMONES INVOLVED IN ENERGY HOMEOSTASIS, AND METHOD AND COMPOSITIONS FOR USE THEREOF

CROSS-REFERENCE TO RELATED APPLICATION

This Application is a Division of application Ser. No. 08/538,816, filed Oct. 3, 1995, which is a continuation-in-part of U.S. application Ser. No. 08/437,466, filed May 9, 1995 now abandoned.

FIELD OF THE INVENTION

The present invention relates generally to receptors for peptide hormones which are involved in regulating glucose and/or insulin levels, i.e., in energy homeostasis.

BACKGROUND OF THE INVENTION

Pituitary adenylate cyclase activating polypeptide (PACAP) is the newest member of the superfamily of metabolic, neuroendocrine and neurotransmitter peptide hormones that exert their action through the cAMP-mediated signal transduction pathway (Arimura, 1992, *Regul. Peptides* 37:287–303). The biologically active peptides are released from the biosynthetic precursor in two molecular forms, either as a 38-amino acid peptide (PACAP-38) and/or as a 27-amino acid peptide (PACAP-27) with an amidated carboxyl termini (Arimura, 1992, *Regul. Peptides* 37:287–303).

The highest concentrations of the two forms of the peptide are found in the brain and testis (reviewed in Arimura, supra). They are also expressed in peripheral tissues, such as adrenal gland, stomach and pancreas (Arimura, supra). The shorter form of the peptide, PACAP-27, shows 68% structural homology to vasoactive intestinal polypeptide (VIP). However, the distribution of PACAP and VIP in the central nervous system suggests that these structurally related peptides have distinct neurotransmitter functions (Koves et al., 1991, *Neuroendocrinology* 54:159–169). Biochemical and cloning experiments have demonstrated that there are receptors which recognize both PACAP and VIP peptides with similar affinities (reviewed in Harmar and Lutz, 1994, *Trends in Pharm. Sci.* 15:97–99), as well as a receptor that is specific for PACAP-38 and PACAP-27 (PACAP-Type 1 receptor) (Christophe, 1993, *Biochim. Biophys. Acta* 1154:183–199; Hashimoto et al., 1993, *Neuron* 11:333–342).

Despite the rapid progress in identifying the PACAP-Type 1 and the common PACAP/VIP receptors, the role of PACAPs in human physiology remain elusive. Furthermore, in view of the finding of common PACAP/VIP receptors some of the physiological functions previously attributed to the VIP will need to be reexamined. Recent studies have demonstrated diverse biological effects of PACAP-38, from a role in reproduction (McArdle, 1994, *Endocrinology* 135:815–817) to ability to stimulate insulin secretion (Yada et al., 1994, *J. Biol. Chem.* 269:1290–1293).

SUMMARY OF THE INVENTION

In its broadest aspect, the present invention extends to an energy homeostasis peptide hormone receptor having the following characteristics:

(a) expression in mammalian adipocytes;

(b) being coupled to a cAMP-mediated signal transduction pathway; and (c) binding to pituitary adenylate cyclase activating polypeptide and vasoactive intestinal peptide.

In a further aspect, the energy homeostasis peptide hormone receptor is also present in the brain, and is widely distributed in peripheral tissues. In one embodiment of the invention, the energy homeostasis peptide hormone receptor is PACAP/VIP R-2, which is distributed in tissues including brain, adipocytes, pancreas, skeletal muscle, stomach, kidney and heart, and in another embodiment, the energy homeostasis peptide hormone receptor is PACAP/VIP R-2B, which is distributed in tissues including brain, adipocytes, skeletal muscle and heart.

In a specific example, the energy homeostasis peptide hormone receptor is encoded by a nucleotide sequence of approximately 1.8 kb, and encodes a protein of approximately 438 amino acids (PACAP/VIP R-2) or 432 amino acids (PACAP/VIP R-2B). In a particular embodiment, the energy homeostasis peptide hormone receptor is PACAP/VIP R-2 or PACAP/VIP R-2B, which bind PACAP-27, PACAP-38, VIP and secretin. A preferred embodiment of the invention, PACAP/VIP R-2, is encoded by the nucleotide sequence of SEQ ID NO:3, and/or is a PACAP-VIP R-2 having the amino acid sequence of SEQ ID NOS:1 or 2. In another preferred embodiment of the invention, the energy homeostasis peptide hormone receptor, PACAP/VIP R-2B, has the amino acid sequence of SEQ ID NO:9, and is encoded by the nucleotide sequence of SEQ ID NOS:8 or 10.

In a still further aspect, the present invention extends to methods of using the energy homeostasis peptide hormone receptor as receptor for a metabolic, neuroendocrine and/or neurotransmitter peptide hormone, to control energy homeostasis, including stimulating insulin secretion, and as a modulator of reproductive function.

In a particular embodiment, the present invention relates to all members of the herein disclosed family of energy homeostasis peptide hormone receptors, which have the characteristics of: (a) expression on mammalian adipocytes; (b) being coupled to the cAMP-mediated signal transduction pathway; and (c) binding to pituitary adenylate cyclase activating polypeptide and vasoactive intestinal peptide.

The present invention also relates to a recombinant DNA molecule or cloned gene, or a degenerate variant thereof, which encodes an energy homeostasis peptide hormone receptor; preferably a nucleic acid molecule, in particular a recombinant DNA molecule or cloned gene, encoding the energy homeostasis peptide hormone receptor and has a nucleotide sequence or is complementary to a DNA sequence shown in FIG. 6 (SEQ ID NO:3), FIG. 7 (SEQ ID NO:8) or FIG. 9 (SEQ ID NOS:3 and 10).

The human and murine DNA sequences of the energy homeostasis peptide hormone receptors of the present invention or portions thereof, may be prepared as probes to screen for complementary sequences and genomic clones in the same or alternate species. The present invention extends to probes so prepared that may be provided for screening cDNA and genomic libraries for the energy homeostasis peptide hormone receptor. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences set forth in FIG. 6 (SEQ ID NO:3), FIG. 7 (SEQ ID NO:8) or FIG. 9 (SEQ ID NOS:3 and 10). Correspondingly, the preparation of antisense RNA and ribozymes are included herein.

The present invention also includes energy homeostasis peptide hormone receptor proteins having the activities noted herein, and that display the amino acid sequences set forth and described above and selected from SEQ ID NOS:1, 2 and 9.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present energy homeostasis peptide hormone receptor(s), and more particularly, the complete DNA sequence determined from the sequences set forth above and in SEQ ID NOS:3, 8 and 10.

According to other preferred features of certain preferred embodiments of the present invention, a recombinant expression system is provided to produce biologically active animal or human energy homeostasis peptide hormone receptor. The concept of the energy homeostasis peptide hormone receptor contemplates that specific molecules exist for correspondingly specific ligands, such as pituitary adenylate cyclase activating polypeptide (PACAP), vasoactive intestinal peptide (VIP) and the like, as described earlier. Accordingly, the exact structure of each energy homeostasis peptide hormone receptor will understandably vary so as to achieve this ligand and activity specificity. It is this specificity and the direct involvement of the energy homeostasis peptide hormone receptor in the chain of events leading to gene activation, that offers the promise of a broad spectrum of diagnostic and therapeutic utilities.

The present invention naturally contemplates several means for preparation of the energy homeostasis peptide hormone receptor, including as illustrated herein known recombinant techniques, and the invention is accordingly intended to cover such synthetic preparations within its scope. The isolation of the cDNA amino acid sequences disclosed herein facilitates the reproduction of the energy homeostasis peptide hormone receptor by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate transcriptional activity of target mammalian cells by interrupting or potentiating the binding of energy homeostasis peptide hormone receptor to its ligand, or by interrupting its coupling to G-proteins, and/or its ability to activate cAMP. In one instance, the test drug could be administered to a cellular sample with the ligand that activates the energy homeostasis peptide hormone receptor, or an extract containing the activated energy homeostasis peptide hormone receptor, to determine its effect upon the binding activity of the energy homeostasis peptide hormone receptor to any chemical sample (including DNA), or to the test drug, by comparison with a control.

The assay system could more importantly be adapted to identify drugs or other entities that are capable of binding to the energy homeostasis peptide hormone receptor, either in the cytoplasm or in the nucleus, thereby inhibiting or potentiating transcriptional activity. Such assay would be useful in the development of drugs that would be specific against particular cellular activity, or that would potentiate such activity, in time or in level of activity. For example, such drugs might be used to modulate glucose levels, or to treat other pathologies, as for example, in making energy homeostasis peptide hormone receptor more potent in stimulating insulin secretion.

In yet a further embodiment, the invention contemplates antagonists of the activity of an energy homeostasis peptide hormone receptor. In particular, an agent or molecule that inhibits the binding of a ligand to the energy homeostasis peptide hormone receptor is provided. In a specific embodiment, the antagonist can be a peptide having the sequence of a portion of a ligand-binding domain of an energy homeostasis peptide hormone receptor.

One of the characteristics of the present energy homeostasis peptide hormone receptor is its ability to bind to its ligand(s) and activate cAMP-mediated signal transduction pathways.

The diagnostic utility of the present invention extends to the use of the present energy homeostasis peptide hormone receptor in assays to screen for decreased levels of expression of the energy homeostasis peptide hormone receptor, in particular where insulin levels are lower than expected or necessary. Because the activity of the cAMP-mediated signal transduction stimulating proteins described herein may be phosphorylated, they can and presumably are dephosphorylated by specific phosphatases. Blocking of the specific phosphatase is therefore an avenue of pharmacological intervention that would potentiate the activity of the energy homeostasis peptide hormone receptor proteins.

The present invention likewise extends to the development of antibodies against the energy homeostasis peptide hormone receptor(s), including naturally raised and recombinantly prepared antibodies. For example, the antibodies could be used to screen expression libraries to obtain the gene or genes that encode the energy homeostasis peptide hormone receptor(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating transcriptional activity.

In particular, antibodies against specifically phosphorylated factors can be selected and are included within the scope of the present invention for their particular ability in following activated protein. Thus, activity of the energy homeostasis peptide hormone receptor or of the specific polypeptides believed to be causally connected thereto may therefore be followed directly by the assay techniques discussed later on, through the use of an appropriately labeled quantity of the energy homeostasis peptide hormone receptor or antibodies or analogs thereof.

Thus, the energy homeostasis peptide hormone receptors, their analogs and/or analogs, and any antagonists or antibodies that may be raised thereto, are capable of use in connection with various diagnostic techniques, including immunoassays, such as a radioimmunoassay, using for example, an antibody to the energy homeostasis peptide hormone receptor that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the energy homeostasis peptide hormone receptor, or to identify drugs or other agents that may mimic or block their activity. The system or test kit may comprise a labeled component prepared by one of the radioactive and/or enzymatic techniques discussed herein, coupling a label to the energy homeostasis peptide hormone receptors, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the energy homeostasis peptide hormone receptor (s), its (or their) subunits, or active fragments thereof, or upon agents or other drugs determined to possess the same activity. A first therapeutic method is associated with the prevention of the manifestations of conditions causally related to or following from the binding activity of the energy homeostasis peptide hormone receptor or its subunits, and comprises administering an agent capable of modulating the production and/or activity of the energy homeostasis peptide hormone receptor or subunits thereof, either individually or in mixture with each other in an amount effective to prevent the development of those conditions in the host. For example, drugs or other binding partners to the energy homeostasis peptide hormone receptor or proteins may be administered to inhibit or potentiate transcriptional activity, as in the potentiation of energy homeostasis peptide hormone receptor in insulin/diabetes therapy. Also, the blockade of the action of specific phosphatases in the dephosphorylation of activated energy homeostasis peptide hormone receptor or proteins presents a method for potentiating the activity of the energy homeostasis peptide hormone receptor or protein that would concomitantly potentiate therapies based on energy homeostasis peptide hormone receptor/protein activation.

More specifically, the therapeutic method generally referred to herein could include the method for the treatment of various pathologies or other cellular dysfunctions and derangements by the administration of pharmaceutical compositions that may comprise effective inhibitors or enhancers of activation of the energy homeostasis peptide hormone receptor or its subunits, or other equally effective drugs developed for instance by a drug screening assay prepared and used in accordance with a further aspect of the present invention. For example, drugs or other binding partners to the energy homeostasis peptide hormone receptor or proteins, as represented by SEQ ID NOS:1, 2 and 9, may be administered to inhibit or potentiate transcriptional activity, as in the potentiation of insulin in diabetes therapy. Also, the blockade of the action of specific phosphatases in the dephosphorylation of activated energy homeostasis peptide hormone receptor or protein presents a method for potentiating the activity of the energy homeostasis peptide hormone receptor that would concomitantly potentiate therapies based on insulin activation.

In particular, the energy homeostasis peptide hormone receptor proteins of whose sequences are presented in SEQ ID NOS:1, 2 and 9 herein, their antibodies, agonists, antagonists, or active fragments thereof, could be prepared in pharmaceutical formulations for administration in instances wherein insulin therapy is appropriate, such as to treat diabetes and reproductive dysfunction. The specificity of the receptor proteins hereof would make it possible to better manage the aftereffects of current diabetes therapy, and would thereby make it possible to apply energy homeostasis peptide hormone receptor as a general anti-diabetic agent.

Accordingly, it is a principal object of the present invention to provide an energy homeostasis peptide hormone receptor and its subunits in purified form that exhibits certain characteristics and activities associated with transcriptional promotion of cellular activity.

It is a further object of the present invention to provide antibodies to the energy homeostasis peptide hormone receptor and its subunits, and methods for their preparation, including recombinant means.

It is a further object of the present invention to provide a method for detecting the presence of the energy homeostasis peptide hormone receptor and its subunits in mammals in which pathological states are suspected to be present.

It is a further object of the present invention to provide a method and associated assay system for screening substances such as drugs, agents and the like, potentially effective in either mimicking the activity or combating the adverse effects of the energy homeostasis peptide hormone receptor and/or its subunits in mammals.

It is a still further object of the present invention to provide a method for the treatment of mammals to control the amount or activity of the energy homeostasis peptide hormone receptor or subunits thereof, so as to alter the adverse consequences of such presence or activity, or where beneficial, to enhance such activity.

It is a still further object of the present invention to provide a method for the treatment of mammals to control the amount or activity of the energy homeostasis peptide hormone receptor or its subunits, so as to treat or avert the adverse consequences of pathological states.

It is a still further object of the present invention to provide pharmaceutical compositions for use in therapeutic methods which comprise or are based upon the energy homeostasis peptide hormone receptor, its subunits, their binding partner(s), or upon agents or drugs that control the production, or that mimic or antagonize the activities of the energy homeostasis peptide hormone receptor.

Other objects and advantages will become apparent to those skilled in the art from a review of the ensuing description which proceeds with reference to the following illustrative drawings.

BRIEF DESCRIPTION OF THE DRAWINGS

FIGS. 1A–1B show the comparison of the deduced amino acid sequences of the human (SEQ ID NO:1) and rat second common receptor (SEQ ID NO:2) for PACAP and VIP (PACAP/VIP R-2). The dots represent identical amino acid residues. The lines on top of the sequences represent the membrane spanning domains (TM1 through TM7).

FIG. 2A shows the competitive binding experiments with recombinant human PACAP/VIP R-2 receptor expressed in CHL cells. Binding of $^{125}I$-VIP (44 pM) in the presence of increasing concentrations of PACAP-38 (closed circles), VIP (closed triangles), PACAP-27 (open circles) and secretin (open squares). Data points represent an average of two separate experiments (n=6). The variation among individual points was 10% (see Materials and Methods). FIG. 2B shows the stimulation of intracellular cAMP levels in CHO cells expressing the recombinant PACAP/VIP R-2 receptor by PACAP-38, VIP, PACAP-27 and secretin. Data points represent an average of two separate determinations (n=6), except for secretin (n=3) (see Materials and Methods). The variation among individual points was 5 %. PACAP-38 (closed circles), VIP (closed triangles), PACAP-27 (open circles) and secretin (open squares).

FIG. 3 shows the tissue distribution of the second common PACAP/VIP R-2 receptor determined by RNase protection assay. A riboprobe synthesized from human PACAP/VIP R-2 receptor cDNA fragment (HAR4) and hybridized with total RNA isolated from human lung, pancreas, brain, kidney, liver, muscle, stomach, heart (50 μg) and adipose (15 μg). The control lane contains a riboprobe added to yeast tRNA (15 μg). The arrows indicates the expected molecular size of the riboprobe (479 bp) and protected RNA:RNA fragment (419 bp).

FIGS. 6A–6C show the nucleotide sequence of human PACAP/VIP R-2 receptor cDNA (SEQ ID NO:3).

FIGS. 7A–7C show the nucleotide sequence of human PACAP/VIP R-2B receptor cDNA (SEQ ID NO:8).

FIGS. 8A–8B show the comparison of amino acid sequences of human PACAP/VIP R-2 (SEQ ID NO:1) and human PACAP/VIP R-2B (SEQ ID NO:9).

FIGS. 9A–9F show the comparison of nucleotide sequences of human PACAP/VIP R-2 (SEQ ID NO:3) and human PACAP/VIP R-2B (SEQ ID NO:10).

DETAILED DESCRIPTION OF THE INVENTION

Figure 2A:
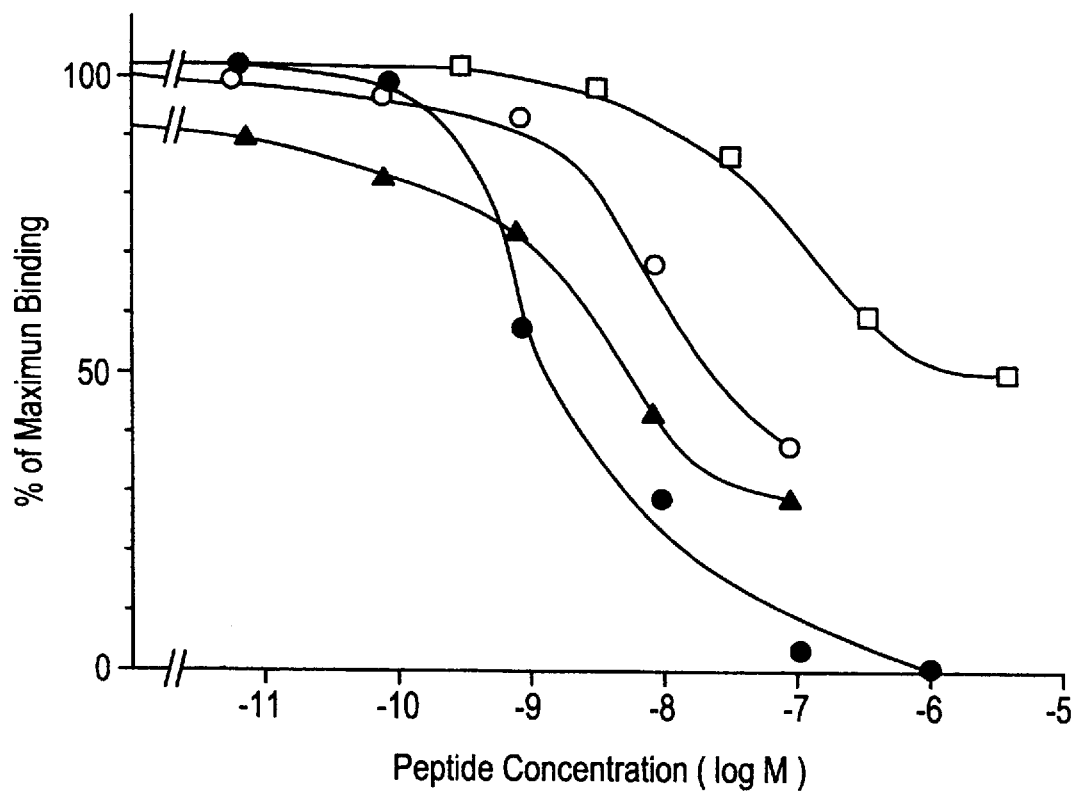
FIGS. 2A–2B.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed.(1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "energy homeostasis peptide hormone receptor", "PACAP/VIP receptor", "second PACAP/VIP receptor", and any variants not specifically listed, may be used herein interchangeably, and as used throughout the present application and claims refer to proteinaceous material including single or multiple proteins, and extends to those proteins having the amino acid sequence data described herein and presented in FIG. 1 (SEQ ID NOS:1 and 2), or FIG. 8 (SEQ ID NOS:1 and 9), and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "energy homeostasis peptide hormone receptor", "PACAP/VIP receptor" and "second PACAP/VIP receptor" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, J. Biol. Chem., 243:3552–59 (1969), abbreviations for amino acid residues are shown in the following Table of Correspondence:

| TABLE OF CORRESPONDENCE | | |
|---|---|---|
| SYMBOL | | AMINO ACID |
| 1-Letter | 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the-terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In its primary aspect, the present invention concerns the identification of an energy homeostasis peptide hormone receptor.

In a particular embodiment, the present invention relates to all members of the herein disclosed PACAP/VIP R-2 and R-2B receptors.

As stated above, the present invention also relates to a recombinant DNA molecule or cloned gene, or a degenerate variant thereof, which encodes an energy homeostasis peptide hormone receptor, or a fragment thereof, that possesses a molecular weight of about 58–64 kD and an amino acid sequence set forth in FIG. 6 (SEQ ID NOS:1 and 2) or FIG. 8 (SEQ ID NOS:1 and 9); preferably a nucleic acid molecule, in particular a recombinant DNA molecule or cloned gene, encoding the about 58–64 kD energy homeostasis peptide hormone receptor has a nucleotide sequence or is complementary to a DNA sequence shown in FIG. 6 (SEQ ID NO:3), FIG. 7 (SEQ ID NO:8) or FIG. 9 (SEQ ID NOS:3 and 10).

The possibilities both diagnostic and therapeutic that are raised by the existence of the energy homeostasis peptide hormone receptor, derive from the fact that when the receptor is occupied by its ligand, other factors thereafter directly interface with a gene and effect transcription and accordingly gene activation. As suggested earlier and elaborated further on herein, the present invention contemplates pharmaceutical intervention in the cascade of reactions in which the energy homeostasis peptide hormone receptor is implicated, to modulate the activity initiated by the stimulus bound to the cellular receptor.

Thus, in instances where it is desired to reduce or inhibit the gene activity resulting from a particular stimulus or factor, an appropriate inhibitor of the energy homeostasis peptide hormone receptor could be introduced to block the interaction of the energy homeostasis peptide hormone receptor with those factors causally connected with gene activation. Correspondingly, instances where insufficient gene activation is taking place could be remedied by the introduction of additional quantities of the energy homeostasis peptide hormone receptor or its chemical or pharmaceutical cognates, analogs, fragments and the like.

As discussed earlier, the energy homeostasis peptide hormone receptors or their binding partners or other ligands or agents exhibiting either mimicry or antagonism to the energy homeostasis peptide hormone receptors or control over their production, may be prepared in pharmaceutical compositions, with a suitable carrier and at a strength effective for administration by various means to a patient experiencing an adverse medical condition associated specific transcriptional stimulation for the treatment thereof. A variety of administrative techniques may be utilized, among them parenteral techniques such as subcutaneous, intravenous and intraperitoneal injections, catheterizations and the like. Average quantities of the energy homeostasis peptide hormone receptors or their subunits may vary and in particular should be based upon the recommendations and prescription of a qualified physician or veterinarian.

Also, antibodies including both polyclonal and monoclonal antibodies, and drugs that modulate the production or activity of the energy homeostasis peptide hormone receptors and/or their subunits may possess certain diagnostic applications and may for example, be utilized for the purpose of detecting and/or measuring conditions such as viral infection or the like. For example, the energy homeostasis peptide hormone receptors or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the energy homeostasis peptide hormone receptors of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against energy homeostasis peptide hormone receptor peptides can be screened for various properties; i.e., isotype, epitope, affinity, etc. Of particular interest are monoclonal antibodies that neutralize the activity of the energy homeostasis peptide hormone receptor or its subunits. Such monoclonals can be readily identified in energy homeostasis peptide hormone receptor activity assays. High affinity antibodies are also useful when immunoaffinity purification of native or recombinant energy homeostasis peptide hormone receptor is possible.

Preferably, the anti-energy homeostasis peptide hormone receptor antibody used in the diagnostic methods of this invention is an affinity purified polyclonal antibody. More preferably, the antibody is a monoclonal antibody (mAb). In addition, it is preferable for the anti-energy homeostasis peptide hormone receptor antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to an energy homeostasis peptide hormone receptor/protein, such as an anti-energy homeostasis peptide hormone receptor antibody, preferably an affinity-purified polyclonal antibody, and more preferably a mAb. In addition, it is preferable for the anti-energy homeostasis peptide hormone receptor antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating the energy homeostasis peptide hormone receptor and inducing anti-energy homeostasis peptide hormone receptor antibodies and for determining and optimizing the ability of anti-energy homeostasis peptide hormone receptor antibodies to assist in the examination of the target cells are all well-known in the art.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in *Antibodies—A Laboratory Manual,* Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with an energy homeostasis peptide hormone receptor-binding portion thereof, or energy homeostasis peptide hormone receptor, or a ligand-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present energy homeostasis peptide hormone receptors and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., *Virol.* 8:396 (1959)) supplemented with 4.5 gm/l glucose, 20 mm glutamine, and 20% fetal calf serum. An exemplary inbred mouse strain is the Balb/c.

Methods for producing monoclonal anti-energy homeostasis peptide hormone receptor antibodies are also well-known in the art. See Niman et al., *Proc. Natl. Acad. Sci. USA,* 80:4949–4953 (1983). Typically, the present energy homeostasis peptide hormone receptor or a peptide analog is used either alone or conjugated to an immunogenic carrier, as the immunogen in the before described procedure for producing anti-energy homeostasis peptide hormone receptor monoclonal antibodies. The hybridomas are screened for the ability to produce an antibody that immunoreacts with the energy homeostasis peptide hormone receptor peptide analog and the present energy homeostasis peptide hormone receptor.

The present invention further contemplates therapeutic compositions useful in practicing the therapeutic methods of this invention. A subject therapeutic composition includes, in admixture, a pharmaceutically acceptable excipient (carrier) and one or more of an energy homeostasis peptide hormone receptor, polypeptide analog thereof or fragment thereof, as described herein as an active ingredient. In a preferred embodiment, the composition comprises an antigen capable of modulating the specific binding of the present energy homeostasis peptide hormone receptor within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of energy homeostasis peptide hormone receptor binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the energy homeostasis peptide hormone receptor/cAMP activator antagonist or analog thereof, and one or more of the following active ingredients: an antibiotic, a steroid. Exemplary formulations are given below:

| Formulations | |
|---|---|
| Intravenous Formulation I | |
| Ingredient | mg/ml |
| cefotaxime | 250.0 |
| energy homeostasis peptide hormone receptor | 10.0 |
| dextrose USP | 45.0 |
| sodium bisulfite USP | 3.2 |
| edetate disodium USP | 0.1 |
| water for injection q.s.a.d. | 1.0ml |
| Intravenous Formulation II | |
| ampicillin | 250.0 |
| energy homeostasis peptide hormone receptor | 10.0 |
| sodium bisulfite USP | 3.2 |
| disodium edetate USP | 0.1 |
| water for injection q.s.a.d. | 1.0ml |
| Intravenous Formulation III | |
| gentamicin (charged as sulfate) | 40.0 |
| energy homeostasis peptide hormone receptor | 10.0 |
| sodium bisulfite USP | 3.2 |
| disodium edetate USP | 0.1 |
| water for injection q.s.a.d. | 1.0ml |
| Intravenous Formulation IV | |
| energy homeostasis peptide hormone receptor | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| energy homeostasis peptide hormone receptor antagonist | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "$\mu$g" mean microgram, "mg" means milligram, "ul" or "$\mu$l" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAS, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosplhoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that energy homeostasis peptide hormone receptor analogs may be prepared from nucleotide sequences of the protein complex/subunit derived within the scope of the present invention. Analogs, such as fragments, may be produced, for example, by pepsin digestion of energy homeostasis peptide hormone receptor material. Other analogs, such as muteins, can be produced by standard site-directed mutagenesis of energy homeostasis peptide hormone receptor coding sequences. Analogs exhibiting "energy homeostasis peptide hormone receptor activity" such as small molecules, whether functioning as promoters or inhibitors, may be identified by known in vivo and/or in vitro assays.

As mentioned above, a DNA sequence encoding energy homeostasis peptide hormone receptor can be prepared synthetically rather than cloned. The DNA sequence can be designed with the appropriate codons for the energy homeostasis peptide hormone receptor amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311(1984).

Synthetic DNA sequences allow convenient construction of genes which will express energy homeostasis peptide hormone receptor analogs or "muteins". Alternatively, DNA encoding muteins can be made by site-directed mutagenesis of native energy homeostasis peptide hormone receptor genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182–188 (April 1989). This method may be used to create analogs with unnatural amino acids.

The present invention extends to the preparation of antisense nucleotides and ribozymes that may be used to interfere with the expression of the energy homeostasis peptide hormone receptor at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into energy homeostasis peptide hormone receptor-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it (Cech, 1988.). Because they are sequence-specific, only mRNAs with particular sequences are inactivated.

Investigators have identified two types of ribozymes, Tetrahymena-type and "hammerhead"-type. (Hasselhoff and Gerlach, 1988) Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for energy homeostasis peptide hormone receptor and their ligands.

The present invention also relates to a variety of diagnostic applications, including methods for detecting the presence of stimuli such as the earlier referenced polypeptide ligands, by reference to their ability to elicit the activities which are mediated by the present energy homeostasis peptide hormone receptor. As mentioned earlier, the energy homeostasis peptide hormone receptor can be used to produce antibodies to itself by a variety of known techniques, and such antibodies could then be isolated and utilized as in tests for the presence of particular transcriptional activity in suspect target cells.

As described in detail above, antibody(ies) to the energy homeostasis peptide hormone receptor can be produced and isolated by standard methods including the well known hybridoma techniques. For convenience, the antibody(ies) to the energy homeostasis peptide hormone receptor will be referred to herein as $Ab_1$ and antibody(ies) raised in another species as $Ab_2$.

The presence of energy homeostasis peptide hormone receptor in cells can be ascertained by the usual immunological procedures applicable to such determinations. A number of useful procedures are known. Three such procedures which are especially useful utilize either the energy homeostasis peptide hormone receptor labeled with a detectable label, antibody $Ab_1$ labeled with a detectable label, or antibody $Ab_2$ labeled with a detectable label. The procedures may be summarized by the following equations wherein the asterisk indicates that the particle is labeled, and "EHPHR" stands for the energy homeostasis peptide hormone receptor:

A. $EHPHR^* + Ab_1 = EHPHR^*Ab_1$

B. $EHPHR + Ab^* = EHPHRAb_1^*$

C. $EHPHR + Ab_1 + Ab_2^* = EHPHRAb_1Ab_2^*$

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody", or "DASP" procedure.

In each instance, the energy homeostasis peptide hormone receptor forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This is because $Ab_1$ raised in one mammalian species has been used in another species as an antigen to raise the antibody $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary or anti-energy homeostasis peptide hormone receptor antibody, and $Ab_2$ will be referred to as a secondary or anti-$Ab_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The energy homeostasis peptide hormone receptor or its binding partner(s) can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the energy homeostasis peptide hormone receptor may be radiolabeled and combined, for example, with antibodies or other inhibitors thereto, after which binding studies would be carried out. Solutions would then be prepared that contain various quantities of labeled and unlabeled uncombined energy homeostasis peptide hormone receptor, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined binding activity or predetermined binding activity capability in suspected target cells. In accordance with the testing techniques discussed above, one class of such kits will contain at least the labeled energy homeostasis peptide hormone receptor or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for predetermined transcriptional activity, comprising:

(a) a predetermined amount of at least one labeled immunochemically reactive component obtained by the direct or indirect attachment of the present energy homeostasis peptide hormone receptor factor or a specific binding partner thereto, to a detectable label;

(b) other reagents; and (c) directions for use of said kit.

More specifically, the diagnostic test kit may comprise:

(a) a known amount of the energy homeostasis peptide hormone receptor as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labeled component which has been obtained by coupling the energy homeostasis peptide hormone receptor to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the energy homeostasis peptide hormone receptor and a specific binding partner thereto.

In accordance with the above, an assay system for screening potential drugs effective to modulate the activity of the energy homeostasis peptide hormone receptor may be prepared. The energy homeostasis peptide hormone receptor may be introduced into a test system, and the prospective drug may also be introduced into the resulting cell culture, and the culture thereafter examined to observe any changes in the transcriptional activity of the cells, due either to the addition of the prospective drug alone, or due to the effect of added quantities of the known energy homeostasis peptide hormone receptor.

To determine whether PACAPs have a broader role in the regulation of insulin-glucose homeostasis, the present invention focuses on identification of PACAP receptors in peripheral tissues which are the sites of glucose turnover. The present invention surprisingly identifies the nucleic acid, amino acid and functional characterization of a second common PACAP/VIP receptor cDNA expressed in human adipocytes. This receptor type (PACAP/VIP R-2) recognizes PACAP-38 and VIP with a higher affinity than PACAP-27. The second common PACAP/VIP (PACAP/VIP R-2) receptor RNA transcripts are also expressed in high levels in human brain and a number of human peripheral tissues, including pancreas, adipocytes, skeletal muscle, stomach, kidney and heart, while PACAP/VIP R-2B is present in brain, adipocytes, muscle and heart, but not pancreas, stomach and kidney.

The extensive differences in the 5'-untranslated regions of PACAP/VIP R-2 and PACAP/VIP R-2B, along with the differential tissue distribution of the R-2 and R-2B receptors indicate that these two receptor subtypes are either encoded by two different genes, or are products of differential splicing of a single gene. Southern blot analysis may be used to distinguish between these two possibilities.

EXAMPLE 1

Materials and Methods

Materials

Human total RNAs and yeast tRNA were obtained from commercial sources (Clontech, Palo Alto, Calif.). Human adipose tissue total RNA was kindly provided by Dr. Susan Fried. Synthetic PACAP-38, PACAP-27, VIP and secretin were purchased from Peninsula, Belmont, Calif.

Methods

1. Cloning and sequencing of a second common PACAP/VIP receptor expressed in human adipose tissue cDNA library $1.8 \times 10^6$ plaques from a human adipose tissue cDNA library in λgt-11 vector (Clontech, Palo Alto, Calif.) were screened with a 32-P labeled rat GLP-I receptor cDNA (Mojsov and Wei, 1993, *Digestion* 54:319–319). Three positive plaques were detected. One of them, that contained a 1.2 kb insert (HAR4) (see Results) was used as a probe to rescreen the same library. Full-length cDNA clone (1.81 kb, HAR 19) was obtained and sequenced. It encoded a novel sequence of a G-protein coupled receptor that was subsequently identified (see below) as a human second common PACAP/ VIP receptor (PACAP/VIP R-2). The sequence has been deposited in the Gene Bank (accession number U18810).

2. Isolation by RT-PCR of cDNA fragments encoding human PACAP-Type 1 and the other common PACAP/VIP (PACAP/VIP R-1) receptors The following primers were used to amplify a 216 bp cDNA fragment of the PACAP-Type 1 receptor: (i) sense: 5'-ATAGTACTGGTCAGCTGCCCTGAGCTC-3' (SEQ ID NO:4) and (ii) antisense:5'-CAGTCTCAGATTCATATTCATC-3' (SEQ ID NO:5). A Sca I site was added into the 5'-end of the sense primer in order to obtain a riboprobe with an appropriate size (see below, 3, (ii)). The amplified fragment corresponds to the extracellular domain of the receptor from nucleotide position 464 to 680 (Ogi et al., 1993, Biochem. Biophys. Res. Comm. 196; 1511–1521).

The following primers were used to amplify a cDNA fragment encoding PACAP/VIP R1: (i) sense: 5'-CAATAGGCTGCAGCAAGATGT-3' (SEQ ID NO:6) and (ii) antisense: 5'-ACAGAACCGTAGAACATGGTC-3' (SEQ ID NO:7). The amplified fragment (246 bp) corresponded to the extracellular domain of the receptor located from nucleotide position 190 to 436 (Couvineau et al., 1994, Biochem. Biophys. Res. Comm. 200:769–776).

The RT-PCR was performed on total RNA (5 $\mu$g) from human brain (Clontech, Palo Alto, Calif.) using Superscript II (GIBCO/BRL, Gaithersburg, Md.). PCR amplifications were carried out for 25 cycles at 94° C. for 60 seconds, 56° C. for 60 seconds and 72° C. for 90 seconds.

3. Synthesis of RNA probes

The cDNA fragments of the three PACAP receptors used as templates for the synthesis of the riboprobes were obtained as follows:

(i) PACAP/VIP R-2 receptor: The HAR4 clone (1.2 kb) that encoded the 3'-end of the receptor was inserted into Bluescript II KS(−) vector. A 479 bp cDNA fragment that served as template for the synthesis of the riboprobe was obtained by digestion with Sca I. This fragment contained 419 bp from the PACAP/VIP R-2 cDNA and 60 bp from the vector.

(ii) PACAP-Type 1 and the common PACAP/VIP R-1 receptors: The 216 bp and 246 bp cDNA fragments from PACAP-Type 1 and PACAP/VIP R-1 receptors, respectively, obtained from RT-PCR amplifications were subcloned into pCRTMII vector (Invitrogen, San Diego, Calif.). Treatment with Sca I gave a 280 bp cDNA fragment that contained 212 bp from PACAP-Type 1 receptor cDNA and 68 bp from the vector. Msc I was used to obtain a 274 bp cDNA fragment that contained 206 bp from the PACAP/VIP R-1 cDNA and 68 bp from the vector.

4. RNase protection assays

The linear DNA templates (1 $\mu$g) were transcribed using standard procedures (Sambrook et al., Molecular Cloning, A Laboratory Manual, Vol. 1, pp.7.71–7.78, Cold Spring Harbor Laboratory Press, U.S.A.). In a typical experiment total RNA (15 $\mu$g or 60 $\mu$g) from human tissues or yeast tRNA (15 $\mu$g) were mixed with approximately 5×10$^5$ cpm of riboprobe under conditions described in (Wei and Mojsov, 1995, FEBS Lett. 358:219–224). The molecular size of the RNA:RNA hybrids was determined by gel electrophoresis and visualized by autoradiography after exposure to an X-ray film for 21 days for PACAP/VIP R-2 (FIG. 3) and for 7 days for PACAP-Type 1 (FIG. 4A) and PACAP/VIP R-1 (FIG. 4B).

The results shown in FIG. 3 are composite of three different hybridization experiments with: (i) total RNA prepared from human lung, pancreas, brain, kidney, liver, muscle and stomach (50 $\mu$g); (ii) total RNA from heart (50 $\mu$g) and (iii) total RNA from adipose tissue (15 $\mu$g) and yeast tRNA (15 $\mu$g). Each hybridization experiment was performed at least twice with newly synthesized riboprobes.

5. Northern blots

Figure 5:
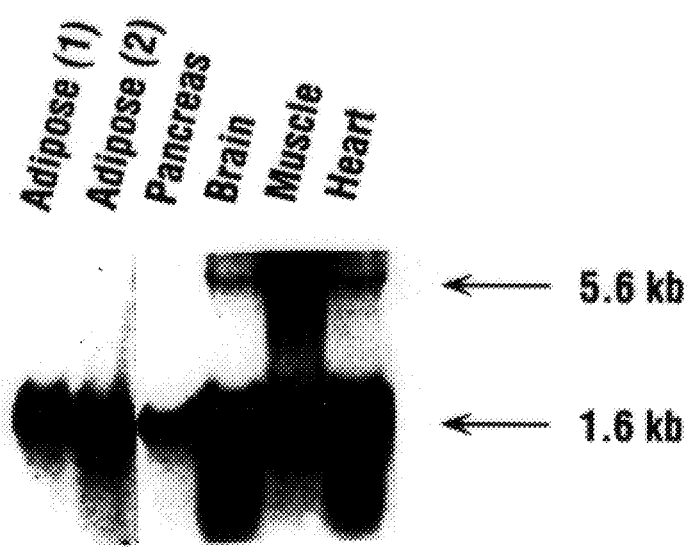
FIG. 5 shows the Northern blot analysis of the second common PACAP/VIP R-2 receptor transcripts. Total RNA (20 μg) was isolated from human adipocytes (1, omental; 2, subcutaneous), pancreas, brain, muscle and heart. The arrows indicate the molecular size of detected transcripts. The figure is a composite of two separate experiments (see Materials and Methods).

Total RNA (20 $\mu$g) from different human tissues was separated on a 1.2% agarose/formamide gel and blotted onto Gene Screen Plus (New England Nuclear, Boston, Mass.). The blot was hybridized with $^{32}$P-labeled HAR 19 cDNA insert for 18 hour under standard conditions (Sambrook et al., Molecular Cloning, A Laboratory Manual, Vol. 1, pp. 7.43–7.78, Cold Spring Harbor Laboratory Press, U.S.A.). The results shown in FIG. 5 are composite of two different experiments. In one set of experiments, Northern blots were performed with RNA isolated from human pancreas, brain, muscle and heart, and in the second one with RNA isolated from human adipocytes (omental and subcutaneous). In each set of experiments ribosomal RNA was run as a control (data not shown). The molecular size of the RNA transcripts was visualized by autoradiography after exposure to an X-ray film. In the composite autoradiograms shown in FIG. 5, the blot containing RNA from adipocytes was exposed to an X-ray film for 7 days, while the blot containing RNA from pancreas, brain, muscle and heart was exposed for 2 days. In preliminary experiments it was found that the relative abundance of PACAP/VIP R-2 RNA transcripts in adipocytes was lower than in the other tissues examined. Thus, longer exposure times were needed for the blot containing RNA from human adipocytes in order to be able to visualize the larger RNA transcript (5.6 kb). For these reasons, Northern blots could not be used for quantitation of the relative abundance of PACAP/VIP R-2 RNA transcripts in these tissues.

6. Expression of the human PACAP/VIP R-2 receptor

The cDNA clone (HAR19) encoding the full length PACAP/VIP R-2 receptor cDNA was subcloned into the Eco RI site of the pcDNA3 expression vector (Invitrogen, San Diego, Calif.), and transfected into Chinese hamster fibroblast cells (CHL, ATCC CCL39) by the calcium phosphate transfection method. Stable transformants were selected in the presence of G418 (0.8 mg/ml, GIBCO/BRL, Gaithersburg, Md.). In the competitive binding experiments $^{125}$I-VIP (2000 Ci/mmol, Amersham, Arlington Heights, Ill.) and/or $^{125}$I-PACAP-27 (2200 Ci/mmol, New England Nuclear, Boston, Mass.) was incubated with the CHL cells in the presence of increasing concentration ($\mu$M–pM) of different peptides for 15–18 hour at 4° C. The assays were preformed at least two times with a newly synthesized $^{125}$I-VIP and $^{125}$I-PACAP-27 in 24-well plates. Each peptide concentration prepared in Hank's balanced salt solution containing 20 mM HEPES, pH 7.4, 0.5% BSA and 0.1 mM phenylmethylsulfonyl-fluoride (PMSF) was added in triplicates to intact cells. Following the incubation, the cells were washed two times with ice-cold PBS, lysed with 1N NaOH, and radioactivity measured in gamma counter. The nonspecific binding was determined in the presence of 1 $\mu$M concentration of VIP and/or PACAP-38. The maximum specific binding was 5%. The variation among triplicate values was 10%.

7. cAMP assays

Figure 2B:
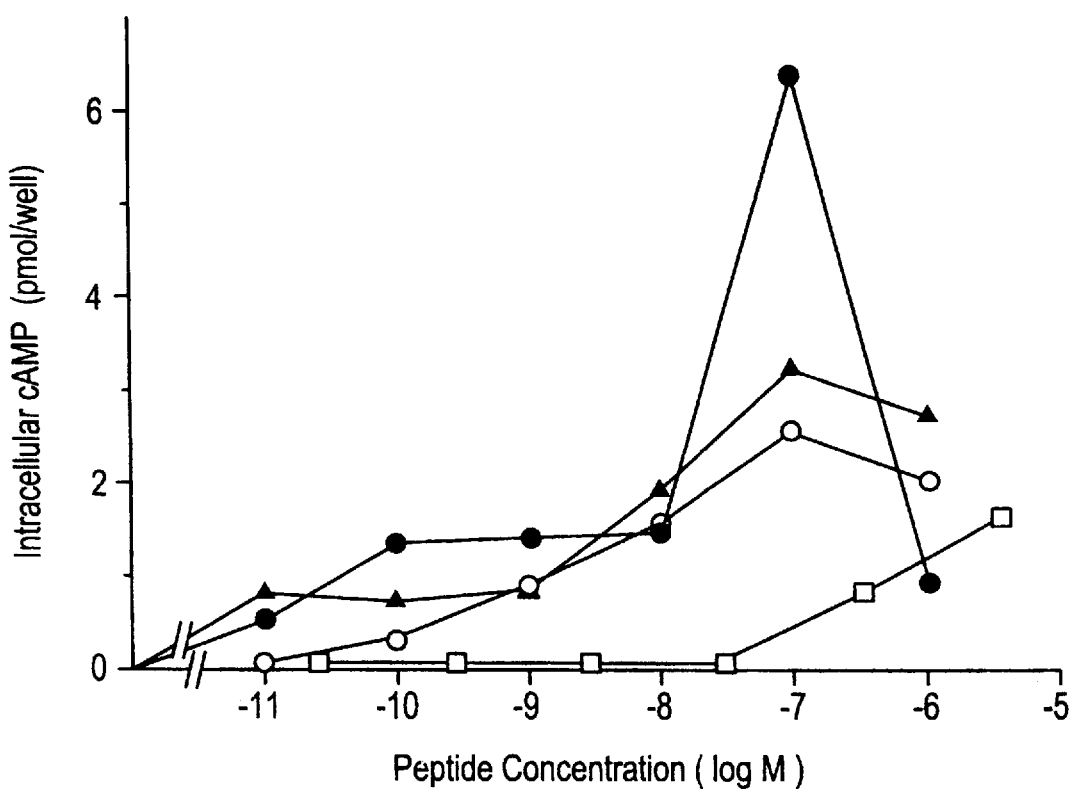

Cells were grown in 24-well plates to about 50% confluence. They were washed twice with the incubation buffer (Macy's 5A pH 7.4, containing 20 mM HEPES, 0.5% BSA and 0.5 mM IBMX) and incubated with different concentration of synthetic peptides added in triplicates (μM–pM) for 45 minutes at 37° C. In each experiment forskolin (10 μM, Sigma, St. Louis, Mo.) was added as a positive control. After removal of the medium, cells were washed twice with PBS and lysed with 95% ethanol. The suspension was centrifuged at 13,000 rpm for 3 minutes, and supernatants were taken to dryness in a speed vacuum. The contents were reconstituted in 0.05M acetate buffer (0.5 ml) and cAMP levels measured using the cAMP Biotrak SPA system (Amersham, Arlington Heights, Ill.). The variation among triplicate values was 5%. The data shown in FIG. 2B are average of two separate incubations (n=6), except for secretin (n=3).

Results

Cloning of a cDNA encoding G-protein coupled receptor expressed in human adipose tissue cDNA library and its functional characterization A human adipose tissue cDNA library was screened and 3 positive plaques were identified, two of which (1.2 kb and 1.3 kb) contained a novel sequence related to the sequences of rat and human GLP-I receptors (Mojsov and Wei, supra; Wei and Mojsov, supra). The 1.2 kb fragment (HAR4) was used in the second round of screening to isolate the full length cDNA. The deduced amino acid sequence (FIG. 1) showed 92% identity to the rat VIP-Type 2 receptor isolated from the olfactory bulb cDNA library (Lutz et al., 1993, *FEBS Let.* 334:3–8) and to PACAP-Type 3 receptor isolated from a mouse insulin-secreting B-cell line cDNA library (Inagaki et al., 1994, *Proc. Natl. Acad. Sci. USA* 91:2679–2683). Its sequence also shows 38% identity to the human GLP-I receptor (Wei and Mojsov, supra), 52% to the human PACAP-Type 1 receptor (Ogi et al., supra) and 49% to the other human common PACAP/VIP receptor (PACAP/VIP R-1) (Couvineau et al., supra).

To further confirm the identity of the receptor, the cDNA was expressed in a chinese hamster lung (CHL) cell line. The recombinant receptor showed slightly higher affinity for PACAP-38 than for VIP, as assessed by competitive binding experiments performed with whole cells maintained in tissue culture (FIG. 2A). The binding of radioiodinated-$^{125}$I-VIP (44 pM) was displaced in a dose dependent manner with PACAP-38 ($ID_{50}$=1.8 nM) and VIP (FIG. 2A). However, in contrast to the displacement curve obtained with PACAP-38, in three separate experiments (n=9) complete displacement of $^{125}$I-VIP binding to the recombinant PACAP/VIP R-2 with high concentrations of unlabeled VIP was not obtainable. Therefore, for VIP the value for the inhibition binding constant could only be estimated ($ID_{50}$=5.8 nM).

Similar results were obtained when $^{125}$I-PACAP-27 (44 pM) was used in the same type of assays. PACAP-38 showed a dose-dependent displacement of $^{125}$I-PACAP-27 binding with $ID_{50=4.1}$ nM, while for VIP the $ID_{50}$ was estimated to be 9 nM (data not shown). In the competitive binding assays $^{125}$I-PACAP-27 had higher non-specific binding than $^{125}$I-VIP, and for these reasons the later compound was used in all binding experiments. $^{125}$I-PACAP-38 was not used in any of the competitive binding experiments.

As seen from FIG. 2A, the shorter PACAP-27 peptide also displaced the binding of $^{125}$I-VIP in a dose dependent manner, but, as it was the case with the VIP displacement curve, complete displacement of $^{125}$I-VIP binding to the recombinant PACAP/VIP R-2 was not obtainable at high PACAP-27 concentration. The estimated $ID_{50}$ was 37 nM. In the same assays secretin, which has high sequence homology to PACAP, as well as VIP, was able to displace at high concentrations (3.8 μM) the binding of $^{125}$I-VIP (FIG. 2A), while glucagon, glucagon-like peptide-I (GLP-I) and glucagon-like peptide-II (GLP-II) did not displace this binding (data not shown). $^{125}$I-VIP did not bind to the CHL cells that were transfected with the vector alone (data not shown).

Incubation of the CHL cells expressing the recombinant human PACAP/VIP R-2 receptor with PACAP-38, PACAP-27 and VIP stimulated intracellular cAMP formation in a dose dependent manner (FIG. 2B). The maximum stimulation of cAMP levels was at 100 nM peptide concentrations. Some increase of intracellular cAMP levels was also observed when the cells expressing the recombinant PACAP/VIP R-2 receptor were incubated with μM concentrations of secretin, while glucagon, GLP-I and GLP-II did not show any stimulation at μM concentrations (data not shown). No change of intracellular cAMP was detected when CHL cells transfected with vector alone were incubated with PACAP-38 (1.1 μM) (data not shown).

Comparison of FIGS. 2A and 2B shows that the dose response curves characterizing the stimulation of intracellular cAMP are shifted towards higher peptide concentrations than the curves characterizing the inhibition of $^{125}$I-VIP binding to CHL cells expressing the recombinant human PACAP/VIP R-2. This effect most likely reflects inefficient coupling of the recombinant PACAP/VIP R-2 to the G-protein(s) present in the CHL cells. In addition, the curve describing PACAP-38 stimulation of intracellular cAMP levels showed a sharp drop to baseline levels at 1 μM concentration of PACAP-38 (FIG. 2B). The observed inhibition of cAMP formation in response to supraphysiological concentration of PACAP-38 might be triggered by ligand specific receptor desensitization. This phenomenon has been described for G-protein coupled receptors (Benovic et al., 1988, *Ann. Rev. Cell Biol.* 4:405–428), including the VIP receptor in human lymphoma SUP T1 cell line (Robberecht et al., 1989, *Peptides* 10:441–446) and GLP-I receptor on the insulinoma HIT T-15 cell line (Fehmann and Habener, 1991, *Endocrinology* 128:2880–2888).

Tissue-specific distribution of the three types of PACAP-receptors

The goal of these studies was to determine the tissue distribution of the common PACAP/VIP R-2 receptor and compare it to the distribution of PACAP-Type 1 and the other common PACAP/VIP R-1 receptors. For this purpose the RNase protection method was used instead of the commonly used Northern blot analysis. The advantage of the RNase protection method (Melton et al., 1984, *Nucl. Acid Res.* 12: 7035–7056) is that it eliminates the cross-reactivities among different types of PACAP/VIP receptors, as well as other structurally related G-protein coupled receptors (Segre and Goldrinr, 1993, *Trends Endocrinol. Metab.* 4:309–314). Use of Northern blot technique may account for some of the inconsistencies and contradictions found in the current literature describing the tissue distribution of the this newly identified family of G-protein coupled receptors. In addition, the RNase protection assay is more sensitive method of detection than the Northern blot analysis (Melton et al., supra).

In the first round of experiments, the tissue distribution of the second common PACAP/VIP R-2 receptor was examined. In these experiments adipose tissue RNA was used as a positive control (FIG. 3).

In the next set of experiments, the expression of PACAP-Type 1 and the common PACAP/VIP R-1 receptor RNA transcripts was examined in the heart and the peripheral tissues which are involved in the maintenance of glucose metabolism. In this set of experiments total RNA isolated from human brain was used as a positive control (FIGS. 4A and B).

Figure 4A:
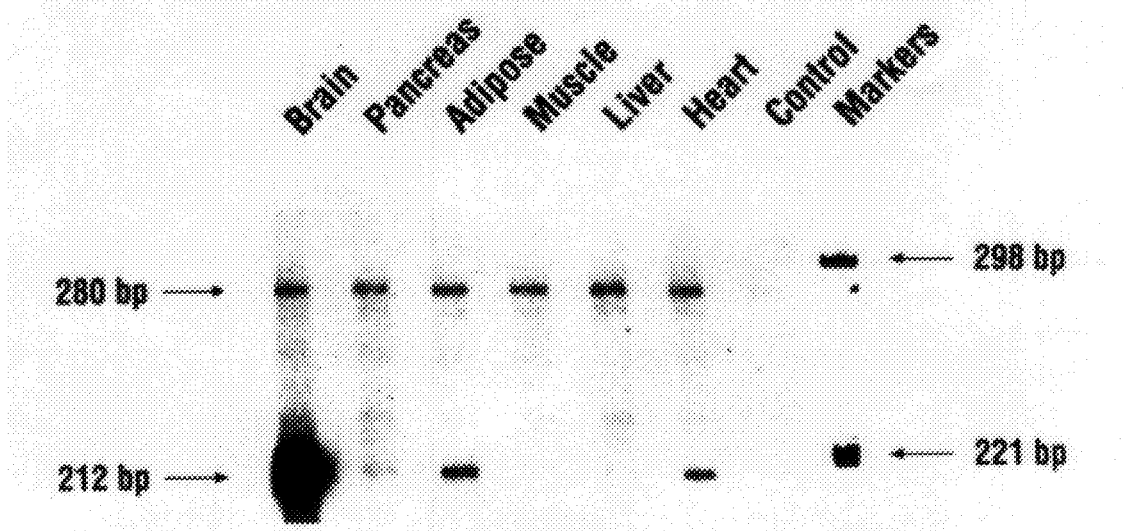
FIGS. 4A–4B show the tissue distribution of PACAP-Type 1 and the other common PACAP/VIP R-1 receptors determined by RNase protection assay. Riboprobes were synthesized from human PACAP-Type 1 (FIG. 4A) and human PACAP/VIP R-1 (FIG. 4B) receptor cDNA fragments (see Materials and Methods) and hybridized with total RNA (15 μg) isolated from human brain, pancreas, adipose, muscle, liver and heart tissues. The control lane contains a riboprobe added to yeast tRNA. The arrows indicate the size of molecular weight markers (221 bp and 298 bp) and the expected size of the riboprobes (274 bp in FIG. 4A, 280 bp in FIG. 4B) and protected receptor fragments. The band representing the riboprobe added to yeast tRNA (control) in FIG. 4B is barely detectable.
Figure 4B:
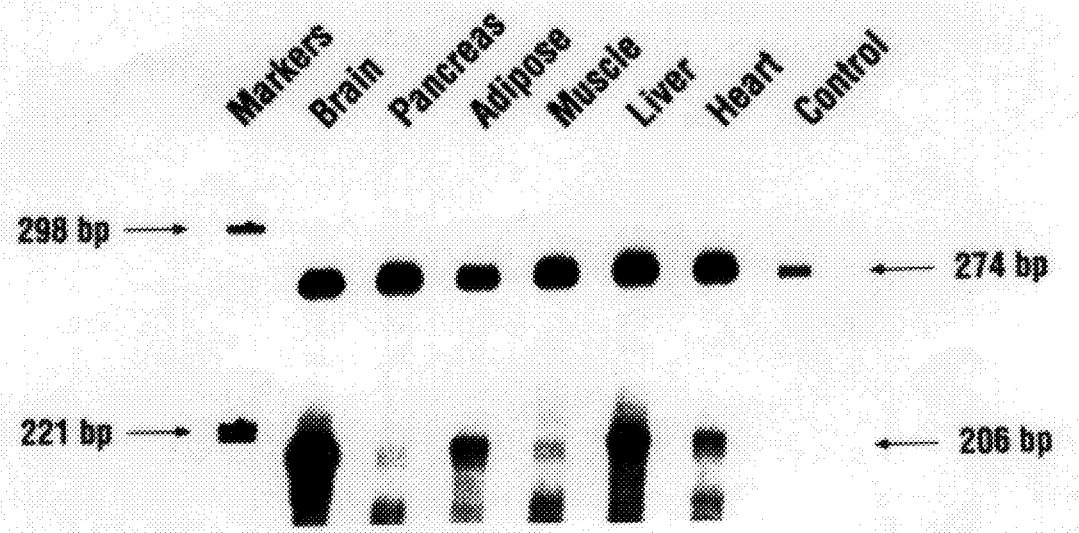

The results shown in FIGS. 3 and 4 (FIGS. 3A and B and 4A and B) clearly demonstrate distinct tissue distribution of the three receptor types. The human heart and adipose tissues contained RNA transcripts for all three types of PACAP receptors. Otherwise, only the second common PACAP/VIP R-2 receptor RNA transcripts are broadly distributed throughout the peripheral tissues, including pancreas and muscle (FIG. 3). The exception is the liver which expresses low levels of this receptor type. In contrast, PACAP/VIP R-1 receptor RNA transcripts were found at high levels in the liver and very low levels in the pancreas and muscle (FIG. 4B). PACAP-Type 1 receptor RNA transcripts were detected at low level in pancreas, muscle and liver (FIG. 4A).

In addition to the expected fragments, some other weak bands were detected, especially in the hybridization experiments with PACAP/VIP R-1 riboprobe (FIG. 3A). They most likely represent an artifact of the RNase protection assay related to the redundancy at ends of the probe (Melton et al., supra).

Northern blot analysis was performed in order to examine the molecular size of PACAP/VIP R-2 RNA transcripts present in different human tissues. In the first set of experiments RNA isolated from brain, heart, pancreas and muscle was included, and in the second set RNA prepared from adipose tissues (omental and subcutaneous) was examined. As seen on FIG. 5, these tissues contain two different RNA transcripts (1.6 kb and 5.6 kb). The larger transcript is uniformly present at much lower levels and is barely detectable in the pancreas and adipose tissues.

Discussion

The results of these studies demonstrate the expression of a second common PACAP/VIP receptor cDNA in human adipose tissue. Its sequence is highly related to sequences of the human PACAP-Type 1 receptor and also to the other common receptor for PACAP and VIP (PACAP/VIP R-1) (Ogi et al., supra; Couvineau et al., supra). The second common PACAP/VIP receptor (PACAP/VIP R-2), like the other two types of PACAP receptors, is also coupled to the cAMP-mediated signal transduction pathway. This receptor is the human homolog (92% identity) of the VIP-Type 2 receptor cDNA cloned from rat olfactory bulb cDNA library (Lutz et al., supra) and PACAP-Type 3 receptor cloned from a mouse insulinoma cell line (Inagaki et al., supra). It has similar binding affinities for PACAP-38 and VIP. In addition to being expressed in the adipose tissue, the human PACAP/VIP R-2 receptor cDNA is also expressed in brain, pancreas, muscle, heart, lung, kidney, stomach and at very low levels in the liver. The wide distribution of PACAP/VIP R-2 receptor suggests that some of the physiological effects of PACAP-38 and VIP in peripheral tissues, especially in pancreas and muscle, are mediated through this receptor type.

In these studies the tissue distributions of PACAP-Type 1 and the other common PACAP/VIP R-1 receptors was examined using RNase protection assays. Results show a distinct distribution of the three PACAP receptor RNA transcripts in peripheral tissues. For example, the human common PACAP/VIP R-1 receptor is the most abundant receptor type expressed in liver, while the human common PACAP/VIP R-2 receptor is expressed at high levels in skeletal muscle and pancreas. These results, taken together with the observation that PACAP-38 stimulates insulin release, indicate a possible role of this peptide in insulin-glucose homeostasis.

The existence of RNA transcripts for the three PACAP-receptors in human adipose tissue indicates other possible physiological roles for PACAPs and VIP. Inasmuch as RNA transcripts for all three PACAP-receptor types are also found in human brain, it is reasonable that PACAP-38 and/or VIP may also be involved in the feedback loop that controls energy homeostasis in human adipocytes and is regulated by the central nervous system. Finally, human heart, like the adipose tissue, also contains RNA transcripts for the three PACAP-receptors.

In the brain the PACAP-Type 1 and the two common PACAP/VIP R-1 and PACAP/VIP R-2 receptors have different anatomical distributions (reviewed in Harmar and Lutz, supra). By analogy, it is likely that in the peripheral tissues the cellular localization of the three PACAP receptors will also be different, allowing each to trigger independent physiological effects.

EXAMPLE 2

Cloning and sequencing of an additional second common PACAP/VIP receptor expressed in human adipose tissue cDNA library A second clone of the second common PACAP/VIP receptor was identified using the methods described in EXAMPLE 1, which encoded a protein having 432 amino acids (SEQ ID NO:9) as shown in FIG. 8, and which was encoded by the nucleotide sequence of SEQ ID NOS:8 and 10 (FIGS. 7 and 9, respectively). RNase protection assays were performed as described above in Example 1, and demonstrated that PACAP/VIP R-2B is present in human brain, adipocytes, muscle and heart, but not in human pancreas, stomach and kidney.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for detecting the presence or activity of an energy homeostasis peptide hormone receptor selected from the group consisting of SEQ ID NO: 1 and SEQ ID NO: 9, said method comprising the steps of:

a) contacting a biological sample from a mammal in which the presence or activity of said energy homeostasis peptide hormone receptor is suspected with a binding partner of said energy homeostasis peptide hormone receptor under conditions that allow binding of said energy homeostasis peptide hormone receptor to said binding partner to occur; and b) detecting whether binding has occurred between said energy homeostasis peptide hormone receptor from said sample and the binding partner;

wherein the detection of binding indicates the presence or activity of said energy homeostasis peptide hormone receptor in said sample.

2. A method for detecting a ligand for an energy homeostasis peptide hormone receptor, said energy homeostasis peptide hormone receptor selected from the group consisting of SEQ ID NO: 1 and SEQ ID NO: 9; said method comprising the steps;

a) placing a labeled energy homeostasis peptide hormone receptor sample in contact with a biological sample from a mammal in which a ligand for said energy homeostasis peptide hormone receptor is suspected;

b) by examining said biological sample in binding studies for the presence of said labeled energy homeostasis peptide hormone receptor;

wherein the presence of said labeled energy homeostasis peptide hormone receptor indicates a ligand for an energy homeostasis peptide hormone receptor.

3. A method for testing the ability of a drug or other agent to modulate the activity of an energy homeostasis peptide hormone receptor selected from the group consisting of SEQ ID NO: 1 and SEQ ID NO: 9 which method comprises:

a) culturing a colony of test cells which has the energy homeostasis peptide hormone receptor in a growth medium containing a ligand for the energy homeostasis peptide hormone receptor;

b) adding the drug or agent under test; and c) measuring the reactivity of said energy homeostasis peptide hormone receptor with the ligand in the growth medium.

4. An assay system for screening drugs and other agents for ability to modulate the production of an energy homeostasis peptide hormone receptor selected from the group consisting of SEQ ID NO: 1 and SEQ ID NO: 9 comprising:

a) culturing an observable test colony inoculated with a drug or agent;

b) harvesting cell membranes from said cellular test colony; and c) examining said membranes for the presence of said energy homeostasis peptide hormone receptor wherein an increase or a decrease in a level of said energy homeostasis peptide hormone receptor indicates the ability of a drug or agent to modulate the activity of said energy homeostasis peptide hormone receptor.

5. A test kit for demonstrating the presence of an energy homeostasis peptide hormone receptor in a eukaryotic cellular sample, comprising:

a) a predetermined amount of an energy homeostasis peptide hormone receptor selected from the group consisting of SEQ ID NO: 1 and SEQ ID NO: 9;

b) a predetermined amount of a specific binding partner of said energy homeostasis peptide hormone receptor; and c) directions for use of said kit;

wherein either said energy homeostasis peptide hormone receptor or said specific binding partner are detectably labeled.

6. The test kit of claim 5 wherein said detectably labeled specific binding partner is selected from the group consisting of polyclonal antibodies to the energy homeostasis peptide hormone receptor or fragments thereof, monoclonal antibodies to the energy homeostasis peptide hormone receptor or fragments thereof, and mixtures thereof.

7. A method of determining the energy homeostasis peptide hormone receptor-related pharmacological activity of a compound comprising:

administering the compound to a mammal;

determining the level of phosphorylated energy homeostasis peptide hormone receptor proteins present where said energy homeostasis peptide hormone receptor is selected from the group consisting of SEQ ID NO: 1 and SEQ ID NO: 9; and comparing the level of energy homeostasis peptide hormone receptor protein phosphate to a standard.

* * * * *